United States Patent
Goto et al.

(10) Patent No.: US 10,395,396 B2
(45) Date of Patent: Aug. 27, 2019

(54) X-RAY CT APPARATUS, RECONFIGURATION ARITHMETIC APPARATUS, AND X-RAY CT IMAGE GENERATION METHOD

(71) Applicant: HITACHI, LTD., Tokyo (JP)

(72) Inventors: Taiga Goto, Tokyo (JP); Hisashi Takahashi, Tokyo (JP); Hideaki Fujii, Tokyo (JP)

(73) Assignee: HITACHI, LTD., Tokyo (JP)

(*) Notice: Subject to any disclaimer, the term of this patent is extended or adjusted under 35 U.S.C. 154(b) by 204 days.

(21) Appl. No.: 15/562,325

(22) PCT Filed: Feb. 29, 2016

(86) PCT No.: PCT/JP2016/055964
§ 371 (c)(1),
(2) Date: Sep. 27, 2017

(87) PCT Pub. No.: WO2016/158138
PCT Pub. Date: Oct. 6, 2016

(65) Prior Publication Data
US 2018/0350113 A1    Dec. 6, 2018

(30) Foreign Application Priority Data

Apr. 1, 2015 (JP) ................. 2015-075322

(51) Int. Cl.
*G06T 11/00*    (2006.01)
*A61B 6/00*    (2006.01)
*A61B 6/03*    (2006.01)

(52) U.S. Cl.
CPC ............ *G06T 11/008* (2013.01); *A61B 6/032* (2013.01); *A61B 6/5258* (2013.01); *A61B 6/5282* (2013.01)

(58) Field of Classification Search
CPC ......... G06T 5/001; G06T 5/002; G06T 5/005; G06T 7/0012; G06T 11/003;
(Continued)

(56) References Cited

U.S. PATENT DOCUMENTS 5,243,664 A    9/1993  Tuy .................................. 382/6
5,841,828 A * 11/1998  Gordon et al. ....... G06T 11/003
                                                                   378/4
(Continued)

FOREIGN PATENT DOCUMENTS

JP    3-222943 A    10/1991    ............... A61B 6/03
JP    8-140964 A     6/1996    ............... A61B 6/03
(Continued)

OTHER PUBLICATIONS

International Search Report dated May 24, 2016 in connection with PCT/JP2016/055964.

*Primary Examiner* — Andrew W Johns
(74) *Attorney, Agent, or Firm* — Cooper & Dunham LLP

(57) ABSTRACT

In order to reduce a metal artifact using a short process, without causing image quality deterioration, when a subject containing metal is imaged in an X-ray CT apparatus, the invention is such that a high frequency component is extracted utilizing the fact that a high frequency component is a structure in error projection data, which are a difference between primary corrected projection data wherein at least one portion of an artifact component caused by metal has been removed and photographed projection data acquired by imaging. The high frequency component, extracted while carrying out weighting in order to suppress the metal artifact, is restored to the primary corrected projection data, after which an image is reconstructed. Also, metal projection data used when compiling the primary corrected projection data are calculated from a value that is a CT value corre- (Continued)

sponding to soft tissue subtracted from a CT value of a metal region.

18 Claims, 11 Drawing Sheets

(58) Field of Classification Search
CPC ......... G06T 11/005; G06T 2207/20182; A61B 6/5258; A61B 6/5282
See application file for complete search history.

(56) References Cited

U.S. PATENT DOCUMENTS

| | | | |
|---|---|---|---|
| 8,233,586 B1 | 7/2012 | Boas | 378/4 |
| 2001/0028696 A1 | 10/2001 | Yamada et al. | 378/4 |
| 2008/0253635 A1 | 10/2008 | Spies et al. | 382/131 |
| 2009/0190814 A1* | 7/2009 | Bouman et al. | G06T 11/006 382/131 |
| 2011/0007956 A1 | 1/2011 | Meyer et al. | 382/131 |
| 2011/0206258 A1 | 8/2011 | Chen et al. | 382/131 |
| 2012/0263360 A1* | 10/2012 | Zhu et al. | G06T 5/002 382/131 |
| 2017/0301066 A1* | 10/2017 | Wang et al. | G06T 7/11 |

FOREIGN PATENT DOCUMENTS

| | | | | |
|---|---|---|---|---|
| JP | 2001-286463 A | 10/2001 | ............... | A61B 6/03 |
| JP | 2004-357969 A | 12/2004 | ............... | A61B 6/03 |
| JP | 2007-520300 A | 7/2007 | ............... | A61B 6/03 |
| JP | 2009-201840 A | 9/2009 | ............... | A61B 6/03 |
| JP | 2011-172926 A | 9/2011 | ............... | A61B 6/03 |

* cited by examiner (a)

(b)

(a)

(b)

(a)

(b)

X-RAY CT APPARATUS, RECONFIGURATION ARITHMETIC APPARATUS, AND X-RAY CT IMAGE GENERATION METHOD

TECHNICAL FIELD

The present invention relates to artifact reduction technology used in an X-ray CT apparatus, and in particular, relates to a reconstruction arithmetic apparatus such that image quality deterioration due to metal artifact reduction technology when imaging a subject including metal does not occur, an X-ray CT apparatus in which the reconstruction arithmetic apparatus is mounted, and an X-ray CT image generation method.

BACKGROUND ART

An X-ray CT apparatus is such that a subject is penetrated, an X-ray attenuated in accordance with an X-ray attenuation coefficient of a substance (composition) inside the penetrated subject is received in an X-ray detector, various kinds of process are carried out in response to an electrical signal obtained, and an X-ray CT image is obtained as a distribution diagram of the X-ray attenuation coefficient of the subject interior. The X-ray used is a polychromatic X-ray, and beam hardening correction in accordance with the substance is carried out.

Metal has high attenuation characteristics differing extremely from those of a substance contained in a normal subject, such as water or bone, and beam hardening has a large effect. Because of this, when metal such as an implant is included in an imaging range, this cannot be dealt with by beam hardening correction for water or bone, and an artifact appears in an image. An artifact caused by metal is a dark band accompanying beam hardening due to metal, or a streak artifact occurring because of a photon insufficiency.

These artifacts caused by metal are collectively called metal artifacts. These metal artifacts do not stop at a metal margin, but also affect a structure distanced from the metal, causing image quality to deteriorate, and causing visibility of a lesion to worsen.

An image reconstruction method that reduces this kind of metal artifact has been proposed (for example, refer to Patent Document 1 and Patent Document 2). The technology of Patent Document 1 is such that a metal portion in photographed projection data is identified by forward projection processing being carried out on a metal portion image extracted from a reconstructed image. Also, a value of peripheral composition or the like is substituted for the metal portion in the reconstructed image, a composition classification image is generated by applying an edge preserving smoothing process such as a bilateral filter to the value, and composition classification projection data are obtained by forward projection processing being carried out on the composition classification image. The metal portion of the photographed projection data is substituted in the composition classification projection data, post-correction projection data wherein the metal artifact has been corrected are obtained, these are subjected to image reconstruction, and the metal portion is added to the reconstructed image obtained, whereby a corrected image is obtained. Also, the technology of Patent Document 2 is such that a metal portion in photographed projection data is identified by forward projection processing being carried out on a metal portion image extracted from a reconstructed image in the same way as in Patent Document 1.

Also, a composition classification image is generated from the reconstructed image by substituting a predetermined value for each composition such as soft tissue, bone, and air, and composition classification projection data are obtained by forward projection processing being carried out on the composition classification image. The composition classification projection data are combined with the photographed projection data in which the metal portion has been identified, post-correction projection data wherein the metal artifact has been corrected are obtained, these are subjected to image reconstruction, and the metal portion is added to the reconstructed image obtained, whereby a corrected image is obtained. When combining, standardized projection data are obtained by a standardization (division) process being carried out on the photographed projection data with the composition classification projection data, and after data of a region corresponding to the metal are linearly interpolated with peripheral data in the standardized projection data, a reverse standardization process (multiplying by the composition classification projection data) is carried out, and image reconstruction is carried out, whereby a corrected image is obtained.

Also, the technologies of Patent Documents 1 and 2 are such that after data of a region corresponding to the metal are linearly interpolated with peripheral data in the photographed projection data, the image is reconstructed, whereby a corrected image is obtained.

CITATION LIST

Patent Literature

Patent Document 1: U.S. Pat. No. 8,233,586 specification
Patent Document 2: U.S. Unexamined Patent Application Publication No. 2011/0007956 specification

SUMMARY OF INVENTION

Technical Problem

According to the technologies of Patent Document 1 and Patent Document 2, image reconstruction is carried out after all tissues coinciding with a metal portion in a sinogram (photographed projection data) are substituted in order to reduce an artifact caused by metal. Substituted data are obtained by forward projection processing being carried out on a composition classification image. The composition classification image is compiled from image data containing an artifact, and information on a structure of composition such as bone hidden by the artifact, or soft tissue that cannot be correctly classified, in the composition classification image is lost. Consequently, information on projection data that penetrates a region in which metal is contained are missing, and information on a structure therein is also lost. Because of this, an effect extends to a structure originally desired to be left in the image, with the structure liable to become unclear in the image, and image quality deteriorates.

The invention, having been contrived with consideration to the heretofore described situation, has an object of reducing a metal artifact using a short process, without causing image quality deterioration, when a subject containing metal is imaged in an X-ray CT apparatus.

Solution to Problem

The invention is such that a high frequency component is extracted utilizing the fact that a high frequency component is a structure in error projection data, which are a difference between primary corrected projection data, wherein at least one portion of an artifact component caused by metal has been removed, and photographed projection data acquired by imaging. Further, the high frequency component, extracted while carrying out weighting in order to suppress the metal artifact, is restored to the primary corrected projection data, after which an image is reconstructed. Also, metal projection data used when compiling the primary corrected projection data are calculated from a value that is a CT value corresponding to soft tissue subtracted from a CT value of a metal region.

Advantageous Effects of Invention

A metal artifact can be reduced using a short process, without causing image quality deterioration, when a subject containing metal is imaged in an X-ray CT apparatus.

DESCRIPTION OF EMBODIMENTS

Figure 1:
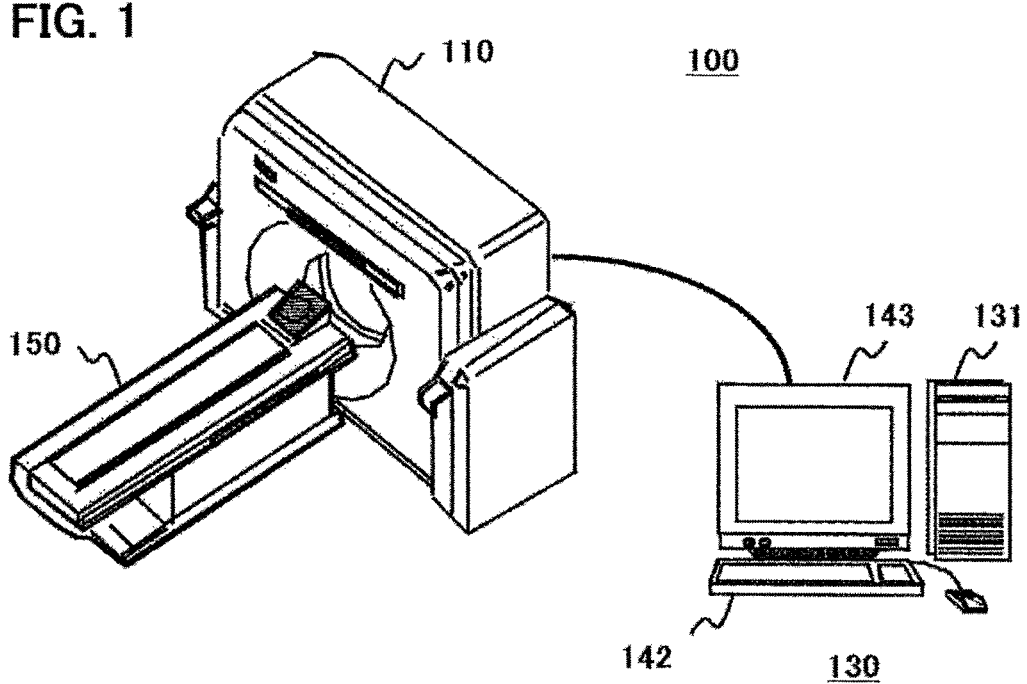
FIG. 1 is an overall external view of an X-ray CT apparatus of a first embodiment.

A reconstruction arithmetic apparatus according to the invention is characterized by including a primary corrected projection data generating unit that generates primary corrected projection data from photographed projection data, which are projection data obtained by a CT scan, by removing at least one portion of an artifact component caused by metal, an error projection data generating unit that subtracts the primary corrected projection data from the photographed projection data, thereby generating error projection data, a high frequency component extracting unit that extracts a high frequency component from the error projection data, and generates the high frequency component as high frequency component projection data, a high frequency component restoring unit that generates secondary corrected projection data by multiplying the high frequency component projection data by a weight in accordance with preset projection data and adding to the primary corrected projection data, and a post-correction image data generating unit that generates post-correction image data based on the secondary corrected projection data.

Also, the reconstruction arithmetic apparatus is characterized in that the primary corrected projection data generating unit includes an initial image data generating unit that generates initial image data from the photographed projection data, a composition classification image data generating unit that generates composition classification image data from the initial image data, a composition classification projection data generating unit that carries out a forward projection on the composition classification image data, thereby generating composition classification projection data, and a metal penetration region substituting unit that substitutes a projected value of a metal penetration region of the photographed projection data with a projected value of the relevant metal penetration region of the composition classification projection data, thereby generating the primary corrected projection data, wherein the composition classification image data generating unit generates the composition classification image data by classifying each pixel of the initial image data into a preset multiple of tissues, and substituting with a preset CT value for each composition.

Also, the reconstruction arithmetic apparatus is characterized in that the initial image data are non-metal image data, and the initial image data generating unit includes a photographed image data generating unit that reconstructs the photographed projection data, thereby generating photographed image data, a metal image data generating unit that generates metal image data obtained by extracting a metal region from the photographed image data, a metal projection data generating unit that carries out a forward projection on the metal image data, thereby generating metal projection data, a non-metal projection data generating unit that carries out an interpolation process on a metal penetration region of the photographed projection data, thereby generating non-metal projection data, and a non-metal image data generating unit that reconstructs the non-metal projection data, thereby generating the non-metal image data, wherein the metal penetration region is a region in which a projected value of the metal projection data is equal to or greater than a predetermined threshold.

Also, the reconstruction arithmetic apparatus is characterized in that the initial image data are photographed image data, and the initial image data generating unit includes a photographed image data generating unit that reconstructs the photographed projection data, thereby generating the photographed image data.

Also, the reconstruction arithmetic apparatus is characterized in that the metal penetration region substituting unit carries out the interpolation process on the metal penetration region of the composition classification projection data, obtains composition classification interpolation projection data, and adds a difference between the composition classification projection data and composition classification interpolation projection data to the non-metal projection data, thereby generating the primary corrected projection data.

Also, the reconstruction arithmetic apparatus is characterized in that the high frequency component extracting unit smooths the error projection data, obtains smoothed error projection data, and subtracts the smoothed error projection data from the error projection data, thereby generating the high frequency component projection data.

Also, the reconstruction arithmetic apparatus is characterized in that the post-correction image data generating unit adds the metal projection data to the secondary corrected projection data, generates post-correction projection data, and obtains the post-correction image data by reconstructing the post-correction projection data.

Also, the reconstruction arithmetic apparatus is characterized in that the post-correction image data generating unit obtains secondary post-correction image data by reconstructing the secondary corrected projection data, and adds a CT value of the metal region of the photographed image data to the secondary post-correction image data, thereby obtaining the post-correction image data.

Also, the reconstruction arithmetic apparatus is characterized by further including an iterative processing unit that substitutes the non-metal projection data with the secondary corrected projection data every time the secondary corrected projection data are generated, and repeats generation of the primary corrected projection data and secondary corrected projection data a preset number of times.

Also, the reconstruction arithmetic apparatus is characterized in that the high frequency component extracting unit uses a smoothing filter when smoothing the error projection data.

Also, the reconstruction arithmetic apparatus is characterized in that the high frequency component extracting unit uses two or more smoothing filters, and the high frequency component restoring unit generates the weight using projection data in accordance with a kind of smoothing filter used.

Also, the reconstruction arithmetic apparatus is characterized in that a value of the weight is set to increase further the further a projected value increases in a predetermined projected value range.

Also, the reconstruction arithmetic apparatus is characterized in that, using a linear value wherein an inverse logarithmic conversion has been carried out on each projected value of the projection data, a value of the weight is set to decrease further the further the linear value increases in a predetermined linear value range.

Also, the reconstruction arithmetic apparatus is characterized in that a reconstruction FOV used when the non-metal image data generating unit generates the non-metal image data is a maximum FOV, and a reconstruction center position is a center of rotation when carrying out the CT scan.

Also, the reconstruction arithmetic apparatus is characterized in that the preset multiple of tissues include air, soft tissue, and metal, and the composition classification image data generating unit substitutes a CT value of an air region classified as the air with an average CT value of the air region, substitutes a CT value of a soft tissue region classified as the soft tissue with an average CT value of the soft tissue region, and substitutes a CT value of a metal region classified as the metal with an average CT value of the soft tissue region.

Also, the reconstruction arithmetic apparatus is characterized in that the preset multiple of tissues include soft tissue and metal, and the composition classification image data generating unit saves a composition structure of a CT value of a soft tissue region classified as the soft tissue and takes the CT value to be a value wherein an oscillation component equal to or lower than a preset threshold has been removed, and takes a CT value of a metal region classified as the metal to be a CT value of the soft tissue.

Also, an X-ray CT apparatus according to the invention is characterized by including an X-ray tube that emits an X-ray, an X-ray detector, disposed in an opposing position across a subject, that detects an X-ray that penetrates the subject, a central controller that controls the X-ray tube and X-ray detector so as to carry out a CT scan on the subject, a signal processor that obtains photographed projection data from an X-ray detected in the X-ray detector, and a reconstruction arithmetic apparatus that generates a reconstructed image from the photographed projection data.

Also, an X-ray CT image generation method according to the invention is characterized by generating primary corrected projection data from photographed projection data, which are projection data obtained by a CT scan, by removing at least one portion of an artifact component caused by metal, subtracting the generated primary corrected projection data from the photographed projection data, thereby generating error projection data, extracting a high frequency component from the error projection data, and generating the high frequency component as high frequency component projection data, generating secondary corrected projection data by multiplying by a weight in accordance with projection data set in advance in the high frequency component projection data, and adding to the primary corrected projection data, and reconstructing post-correction image data based on the secondary corrected projection data.

First Embodiment

Hereafter, using the attached drawings, a first embodiment of the invention will be described. In all drawings illustrating embodiments, the same reference signs are allotted to portions having the same function, and a repeated description thereof is omitted, unless otherwise stated.

(X-ray CT Apparatus)

Firstly, an X-ray CT apparatus of the embodiment will be described. FIG. 1 is an external view of an X-ray CT apparatus (multi-slice CT apparatus) 100 of the embodiment. The X-ray CT apparatus 100 of the embodiment includes a scanner 110 used for photography, a bed 150 on which a subject 101 is placed and moved, and an operating unit 130 that processes data acquired using the scanner, and functions as a user interface. The scanner 110, in accordance with an instruction from the operating unit 130, carries out a scanning process (photography) on the subject 101 positioned on the bed 150.

Figure 2:
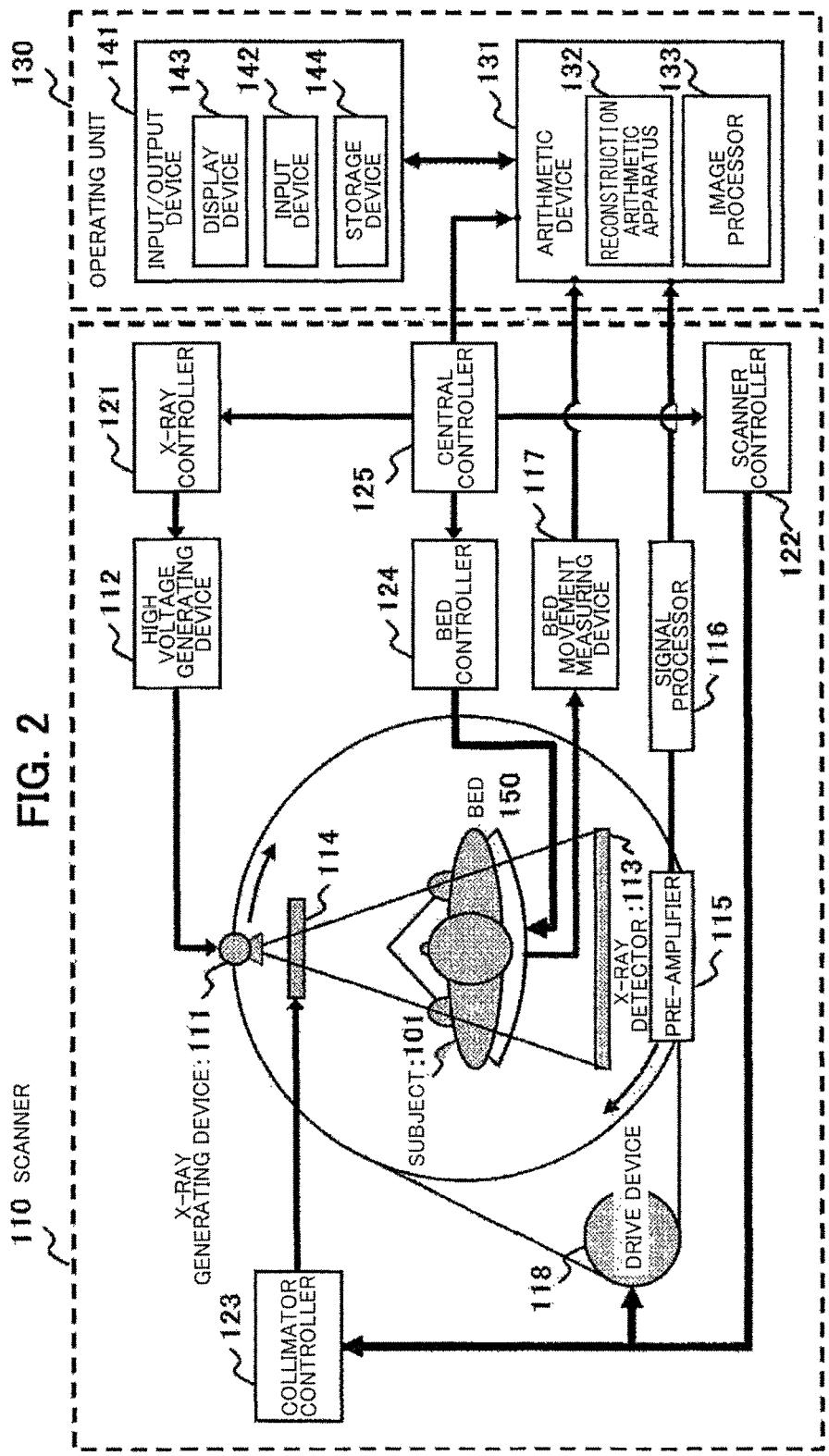
FIG. 2 is a functional configuration diagram of the X-ray CT apparatus of the first embodiment.

FIG. 2 is a functional configuration diagram of the X-ray CT apparatus 100 of the embodiment. A scanning method is a rotate-rotate method (third generation), and is largely configured of the scanner 110, operating unit 130, and bed 150, as shown in FIG. 1.

The scanner 110 includes an X-ray generating device (X-ray tube) 111, a high voltage generating device 112, an X-ray detector 113, a collimator 114, a pre-amplifier 115, a signal processor 116, a bed movement measuring device 117, a drive device 118, an X-ray controller 121, a scanner controller 122, a collimator controller 123, a bed controller 124, and a central controller 125.

Also, the operating unit 130 includes an arithmetic device 131 and an input/output device 141. The arithmetic device 131 includes a reconstruction arithmetic apparatus 132 and an image processor 133, and the input/output device 141 includes an input device 142, a display device 143, and a storage device 144.

The input device 142 is configured of a mouse, a keyboard, and the like, and is used for inputting measurement and reconstruction parameters such as bed movement speed information and a reconstruction position. The display device 143 is configured of a display and the like, and displays a reconstructed image (CT image). The image processor 133 processes a CT image obtained using the reconstruction arithmetic apparatus 132 as necessary.

Imaging conditions (bed movement speed, tube current, tube voltage, slicing position, and the like), reconstruction parameters (region of interest, reconstructed image size, reverse projection phase width, reconstruction filter function, and the like), and various kinds of instruction are input from the input device 142. A control signal necessary for imaging is sent from the central controller 125 to the X-ray controller 121, bed controller 124, and scanner controller 122 based on an input imaging condition, reconstruction parameter, and instruction, an imaging start signal is received, and imaging is started.

When imaging is started, a control signal is sent by the X-ray controller 121 to the high voltage generating device 112 based on the input imaging condition, and a high voltage (tube voltage) is applied to the X-ray generating device 111. Further, electrons of an energy in accordance with the high voltage applied are discharged from a cathode, and the discharged electrons collide with a target (anode), whereby an X-ray of an energy in accordance with the electron energy is emitted from an X-ray source of the X-ray generating device 111 (X-ray tube) to the subject 101.

At the same time, a control signal is sent from the scanner controller 122 to the drive device 118, and the X-ray generating device 111, X-ray detector 113, pre-amplifier 115, and the like, are caused to revolve around the subject 101. That is, the scanner controller 122, in accordance with an instruction from the central controller 125, controls the X-ray generating device 111 and X-ray detector 113 so as to carry out a CT scan on the subject 101. Meanwhile, the bed 150 on which the subject 101 is placed is caused to remain still (when carrying out a normal scan) or caused to move in parallel to a body axis direction (when carrying out a spiral scan) by the bed controller 124.

The emitted X-ray, an irradiated region being limited by the collimator 114, is absorbed (attenuated) by each composition inside the subject 101, penetrates the subject 101, and is detected by the X-ray detector 113. At this time, the X-ray attenuated in accordance with an X-ray attenuation coefficient of a substance (composition) inside the penetrated subject 101 is received (detected) by the X-ray detector 113 disposed in a position opposing the X-ray source.

The X-ray detected by the X-ray detector 113 is converted into current (an electrical signal), amplified by the pre-amplifier 115, converted into digital data (X-ray attenuation data) by the signal processor 116, which includes an A/D converter, various kinds of correction process, logarithm (LOG) conversion process, and the like, are carried out, and the digital data are input into an arithmetic device 131 as projection data. That is, the signal processor 116 generates projection data from an X-ray detected by the X-ray detector 113. The kinds of process carried out by the signal processor 116 include, for example, a reference correction process, calibration, and the like.

The projection data input into the arithmetic device 131 are subjected to an image reconstruction process by the reconstruction arithmetic apparatus 132 in the arithmetic device 131. For example, filter-corrected projection data are obtained by a reconstruction filter being superimposed on the projection data. Further, a reconstructed image is obtained by a reconstruction process being carried out on the filter-corrected projection data. The reconstructed image is a distribution diagram of the X-ray attenuation coefficient of the interior of the subject 101, and is a tomographic image obtained non-destructively. Hereafter, projection data generated by the signal processor 116 and input into the arithmetic device 131 will be called photographed projection data.

The reconstructed image obtained is saved in the storage device 144 in the input/output device 141, and displayed as a CT image on the display device 143. Alternatively, the reconstructed image is displayed as a CT image on the display device 143 after being processed by the image processor 133.

Each kind of controller, beginning with the central controller 125, of the scanner 110, and the arithmetic device 131, include a CPU, a memory, and a storage device. Further, each function realized thereby is realized by a program stored in the storage device 144 being loaded into the memory and executed by the CPU. Also, all or one portion of the functions may be realized by hardware such as an ASIC (application specific integrated circuit) or FPGA (field-programmable gate array). Various kinds of data used in processing the functions, and various kinds of data generated during processing, are stored in the storage device 144.

Herein, the X-ray CT apparatus 100 often uses polychromatic X-ray when photographing. If an image is formed without correcting when using a polychromatic X-ray, shading occurs in the reconstructed image obtained due to the effect of beam hardening. This is because there is a premise that an image reconstruction process with a CT has projection data photographed with a monochromatic X-ray as a target, that is, that the attenuation coefficient does not change in accordance with the substance.

A general X-ray CT apparatus is such that a process of correcting the effect of water or bone beam hardening is incorporated in the image reconstruction process. For example, as soft tissue, which occupies a greater portion of the subject 101, has attenuation characteristics similar to those of water, beam hardening correction with respect to water is carried out, thereby correcting a beam hardening effect such as shading for the subject 101. Also, when a large amount of bone, whose attenuation characteristics differ greatly from those of water, is contained in the subject 101, the bone is extracted from the reconstructed image, and beam hardening correction is carried out in accordance with a projected amount of the extracted bone, thereby restricting an effect such as a dark band caused by the bone.

However, as heretofore described, when a substance having high attenuation characteristics differing extremely from those of water and bone, such as metal used in an implant, is contained in the subject 101, image quality deterioration cannot be restricted by a beam hardening correction with respect to water or bone.

Figure 3:
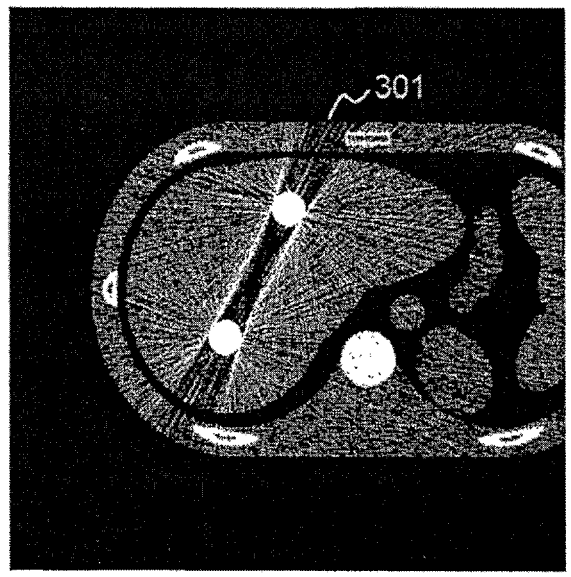
FIG. 3(a) is an illustration for describing an example of a reconstructed image reconstructed using an existing method.
FIG. 3(b) is an illustration for describing an example of a reconstructed image reconstructed using a method of the first embodiment.
Figure 3:
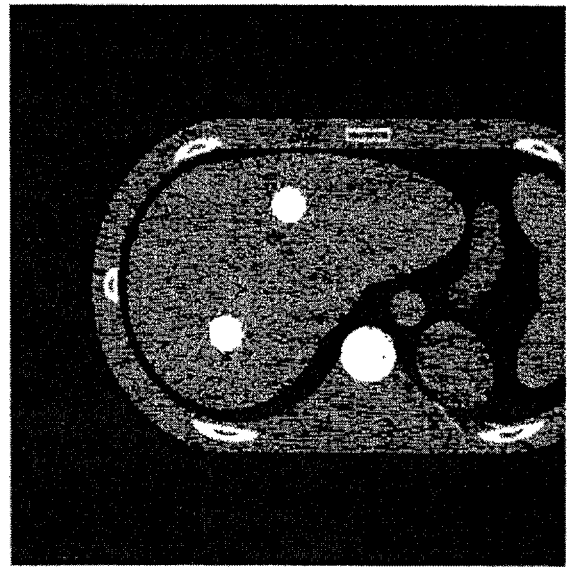

For example, dark bands accompanying beam hardening caused by scattered rays or metal, and streak artifacts occurring because of a photon insufficiency, occur in a reconstructed image 300, as shown in FIG. 3(a). Hereafter, these artifacts caused by metal occurring in a subject image will be collectively called a metal artifact 301. This metal artifact does not stop at a metal margin, but also affects a structure distanced from the metal, causing visibility of a lesion to worsen.

As heretofore described, the method disclosed in Patent Document 1 or Patent Document 2 is such that a metal artifact is removed, but together with this, structure information is lost, and image quality deteriorates. In this embodiment, a metal artifact is reduced while leaving a structure originally desired to be left in the image, that is, restricting deterioration of the structure.

In order to realize this, the reconstruction arithmetic apparatus 132 of this embodiment carries out an image reconstruction process of correcting by carrying out various kinds of process on a projection data signal (hereafter called photographed projection data) output from the signal processor 116, thereby restricting image quality deterioration to a minimum, and obtaining a reconstructed image (CT image) from which a metal artifact has been removed.

When carrying out the image reconstruction process, the reconstruction arithmetic apparatus 132, in order to correct a CT image in which a metal artifact is included, substitutes a place corresponding to metal in the photographed projection data with projection data wherein at least one portion of a metal artifact component has been reduced. Also, a high frequency component of an interpolated place is extracted from data on the difference between the projection data after substitution and the photographed projection data, and restored to the projection data after substitution in accordance with the strength of the metal artifact. Hereafter, details of the reconstruction process of the reconstruction arithmetic apparatus 132 of this embodiment will be described.

(Reconstruction Arithmetic Apparatus)

Firstly, a functional configuration of the reconstruction arithmetic apparatus 132 of this embodiment, which realizes the heretofore described process, will be described.

Figure 4:
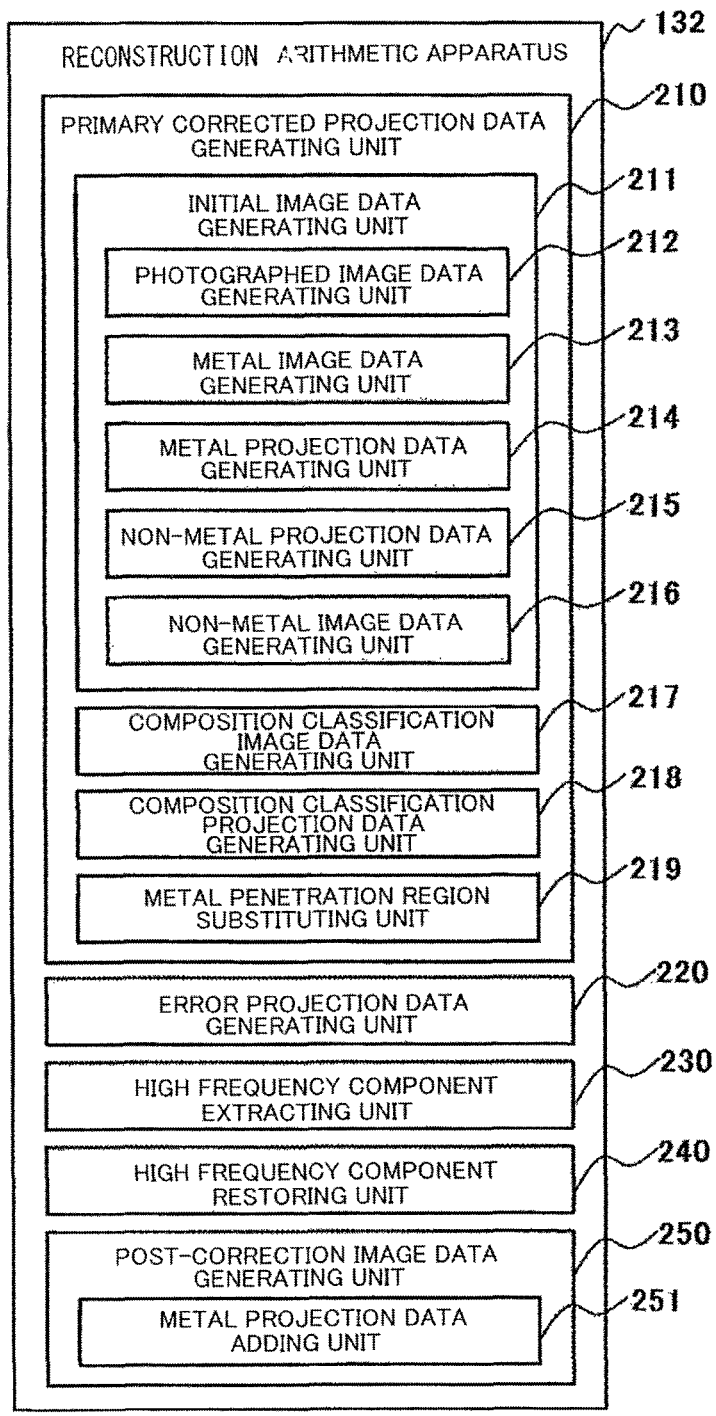
FIG. 4 is a functional block diagram of a reconstruction arithmetic apparatus of the first embodiment.

As shown in FIG. 4, the reconstruction arithmetic apparatus 132 of this embodiment includes a primary corrected projection data generating unit 210 that generates primary corrected projection data from photographed projection data by removing at least one portion of an artifact component caused by metal, an error projection data generating unit 220 that subtracts the primary corrected projection data from the photographed projection data, thereby generating error projection data, a high frequency component extracting unit 230 that extracts a high frequency component from the error projection data, and generates the high frequency component as high frequency component projection data, a high frequency component restoring unit 240 that generates secondary corrected projection data by multiplying the high frequency component projection data by a weight in accordance with preset projection data and adding to the primary corrected projection data, and a post-correction image data generating unit 250 that generates post-correction image data based on the secondary corrected projection data.

Also, the primary corrected projection data generating unit 210 of this embodiment includes an initial image data generating unit 211 that generates initial image data from the photographed projection data, a composition classification image data generating unit 217 that generates composition classification image data from the photographed image data, a composition classification projection data generating unit 218 that carries out a forward projection on the composition classification image data, thereby generating composition classification projection data, and a metal penetration region substituting unit 219 that substitutes a projected value of a metal penetration region of the photographed projection data with a projected value of the a metal penetration region of the composition classification projection data, thereby generating the primary corrected projection data, wherein the composition classification image data generating unit 217 generates the composition classification image data by classifying each pixel of the initial image data into a preset multiple of tissues, and substituting with a preset CT value for each composition.

The initial image data are non-metal image data, and the initial image data generating unit 211 includes a photographed image data generating unit 212 that reconstructs the photographed projection data, thereby generating photographed image data, a metal image data generating unit 213 that generates metal image data obtained by extracting a metal region from the photographed image data, a metal projection data generating unit 214 that carries out a forward projection on the metal image data, thereby generating metal projection data, a non-metal projection data generating unit 215 that carries out an interpolation process on a metal penetration region of the photographed projection data, thereby generating non-metal projection data, and a non-metal image data generating unit 216 that reconstructs the non-metal projection data, thereby generating the non-metal image data. At this time, the metal penetration region is a region in which a projected value of the metal projection data is equal to or greater than a predetermined threshold.

Furthermore, the post-correction image data generating unit 250 includes a metal projection data adding unit 251 that adds the metal projection data to the secondary corrected projection data and generates post-correction projection data, and obtains the post-correction image data by reconstructing the post-correction projection data.

Figure 5:
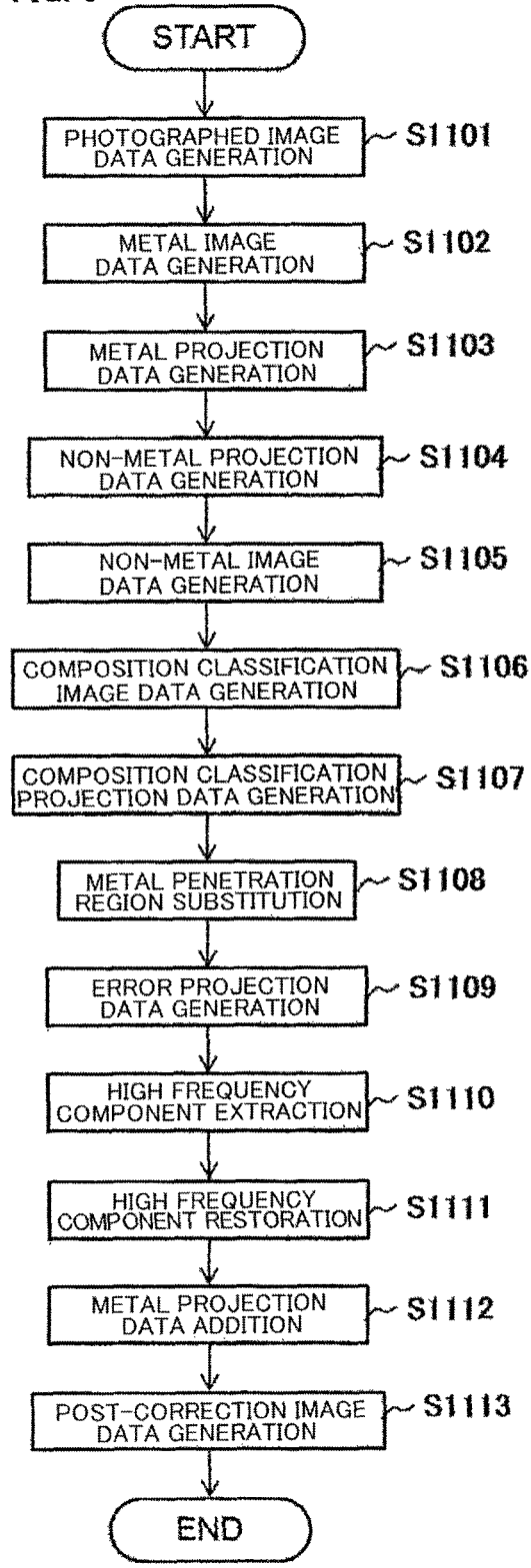
FIG. 5 is a flowchart of a reconstruction process of the first embodiment.
Figure 6:
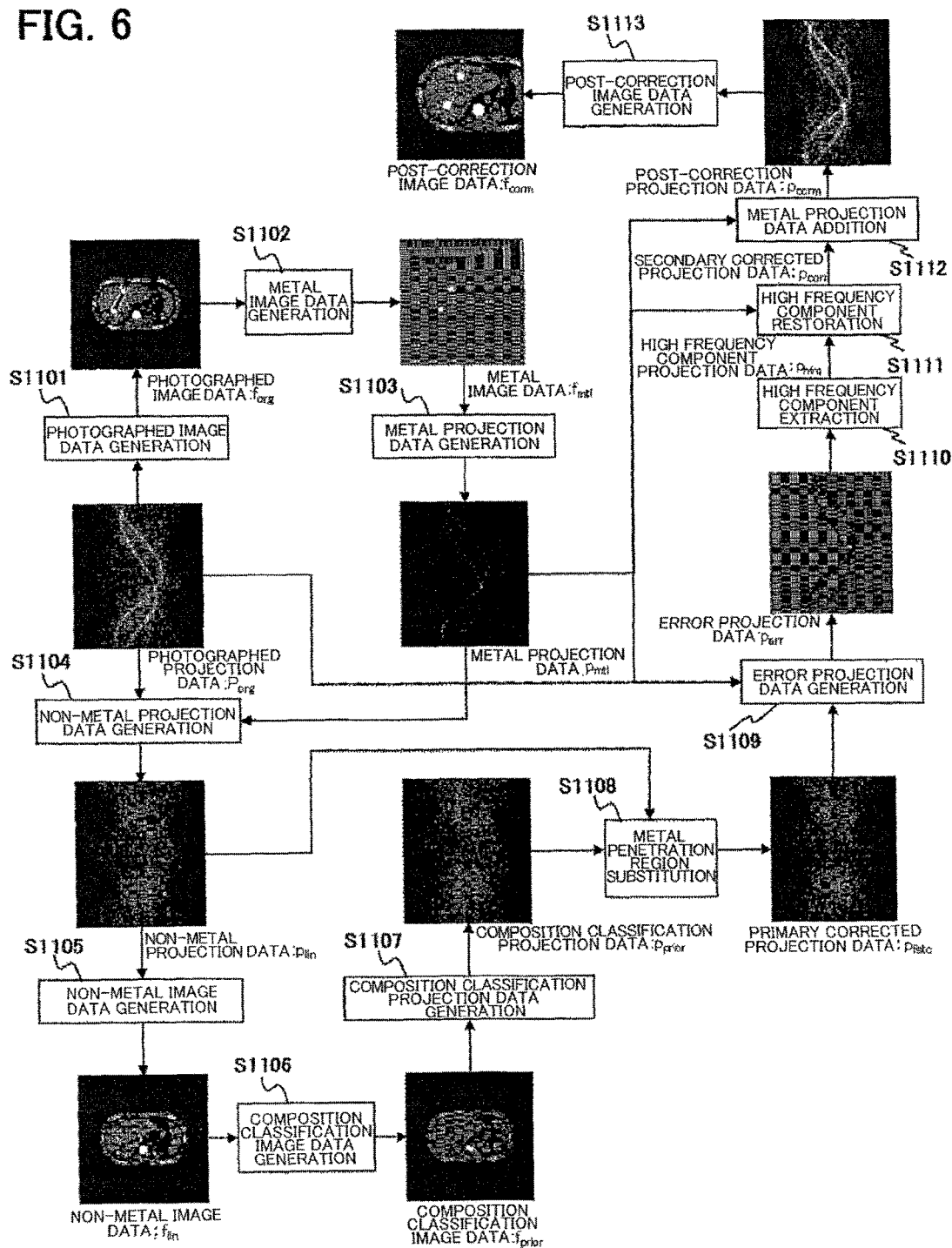
FIG. 6 is an illustration for describing the reconstruction process of the first embodiment.

Hereafter, details of a process of each unit will be described using FIG. 5 and FIG. 6. FIG. 5 is a process flow of a reconstruction process accompanying a correction of a metal artifact by the reconstruction arithmetic apparatus 132 of this embodiment, and FIG. 6 is an illustration for describing the flow of the reconstruction process. Hereafter, each pixel value of the image data will be called a CT value, and a value of a position corresponding to each detected element of the projection data will be called a projected value. Also, a process of generating image data from projection data will be called a reconstruction, and a process of generating projection data from image data will be called a forward projection. Also, in FIG. 6, image data are described as image, and projection data as projection.

(Photographed Image Data Reconstruction Process)

Firstly, the photographed image data generating unit 212 carries out a photographed image data generating process (step S1101). In the photographed image data generating process, the photographed image data generating unit 212 carries out an image reconstruction process $R^{-1}$ on photographed projection data $p_{org}$, thereby generating photographed image data $f_{org}$, as shown in Expression (1) below. For example, an inverse Radon transform, or the like, is used in the image reconstruction process $R^{-1}$.

$$f_{org}=R^{-1}(p_{org}) \quad (1)$$

At this time, a reconstruction FOV is taken to be a full FOV, a reconstruction center is taken to be a center of rotation, and a reconstruction filter is taken to be an abdomen-portion filter. By reconstructing with a full FOV in this way, a metal region of the whole of the subject 101 can be taken into consideration, and even when there is metal not included in the reconstruction FOV, an artifact caused by the metal can be corrected. Herein, a full FOV means an FOV size that encompasses the whole of the subject.

Herein, when it is clear that a region to be photographed is small, such as a head portion, the reconstruction FOV is desirably set small to an extent such that the region to be photographed (for example, the head portion) is included. This switch can be carried out in accordance with a subject size and center of gravity estimated from the projection data and bed height, the reconstruction filter (head portion-use, abdomen portion-use, heart-use, or the like), and photography protocol (abdomen portion, head portion, pelvis, and the like).

(Metal Image Data Generating Process)

Next, the metal image data generating unit 213 carries out a metal image data generating process (step S1102). In the metal image data generating process, only a metal portion is extracted from the photographed image data $f_{org}$, and furthermore, a CT value $v_{sft}$ corresponding to soft tissue is subtracted, thereby generating metal image data $f_{mtl}$, as shown in Expression (2) below.

$$f_{mtl} = E_{mtl}(f_{org}) - v_{sft} \tag{2}$$

Herein, $E_{mtl}$ indicates a metal region segmentation process, and is realized by, for example, a threshold process or the like.

Herein, the CT value $v_{sft}$ corresponding to soft tissue is subtracted in order that a projected value does not reach a maximum when adding metal projection data in a metal projection data adding process carried out by the metal projection data adding unit 251, to be described hereafter. The maximum is reached because a metal region of composition classification projection data, which forms abase when adding metal projection data in the metal projection data adding process to be described hereafter, has a projected value corresponding to soft tissue rather than air.

Metal projection data that take beam hardening into consideration may be used. At this time, specifically, correction is carried out based on a relational expression between a measured projected value of metal of a known size and an ideal projected value calculated by simulation, in the same way as an existing water or bone beam hardening correction.

(Metal Projection Data Generating Process)

When the metal image data $f_{mtl}$ are generated, the metal projection data generating unit 214 carries out a metal projection data generating process (step S1103). The metal projection data generating unit 214 carries out a forward projection process R on the metal image data $f_{mtl}$, thereby generating metal projection data $p_{mtl}$, as shown in Expression (3) below.

$$p_{mtl} = R(f_{mtl}) \tag{3}$$

The forward projection process R is realized by, for example, a Radon transform or the like.

(Non-metal Projection Data Generating Process)

When the metal projection data $p_{mtl}$ are generated, the non-metal projection data generating unit 215 carries out a non-metal projection data generating process of interpolating with a projected value neighboring a metal penetration region in the projection data, thereby generating non-metal projection data (step S1104).

Firstly, the non-metal projection data generating unit 215 identifies a region in the metal projection data $p_{mtl}$ whose projected value is equal to or greater than a preset threshold as a metal penetration region in the projection data. The metal penetration region is a region in which an X-ray that has penetrated a metal region of the subject 101 is detected by the X-ray detector 113. Further, the non-metal projection data generating unit 215 carries out an interpolation process M on a metal penetration region in the photographed projection data $p_{org}$, thereby generating non-metal projection data $p_{Lin}$, as shown in Expression (4).

$$P_{Lin} = M(P_{org}) \tag{4}$$

The interpolation process is carried out by linear interpolation using data of regions that do not exceed the threshold neighboring either end portion in a channel direction of the metal penetration region, which is a data portion exceeding the threshold. Also, the threshold used when identifying the metal penetration region is, for example, 1.0.

(Non-metal Image Data Generating Unit)

When the non-metal projection data $p_{Lin}$ are generated, the non-metal image data generating unit 216 carries out a non-metal image data generating process (step S1105). The non-metal image data generating unit 216 carries out the image reconstruction process $R^{-1}$ on the non-metal projection data $p_{Lin}$, thereby generating non-metal image data $f_{Lin}$ from which the metal has been removed, as shown in Expression (5) below.

$$f_{Lin} = R^{-1}(p_{Lin}) \tag{5}$$

At this time, an image reconstruction process is carried out taking the reconstruction FOV to be a full FOV and the reconstruction center to be the center of rotation, in the same way as in the photographed image data generating process, and a filter with comparatively little noise, for example, an abdomen portion-use filter, is used as the reconstruction filter. The center of rotation is the center of rotation of the X-ray generating device 111 and X-ray detector 113 when carrying out a CT scan. Herein, when it is clear that a region to be photographed is small, such as a head portion, the reconstruction FOV is desirably set small to an extent such that the region to be photographed (for example, the head portion) is included. This switch can be carried out in accordance with a subject size and center of gravity estimated from the projection data and bed height, the reconstruction filter (head portion-use, abdomen portion-use, heart-use, or the like), and photography protocol (abdomen portion, head portion, pelvis, and the like).

By reconstructing with a full FOV in this way, the non-metal image data $f_{Lin}$ can be generated to include the whole of the subject 101. Because of this, composition classification projection data having a value near photographed projection data with no protrusion of the subject 101 can be generated in a composition classification projection data generating process to be described hereafter. Consequently, a metal artifact can be corrected with high accuracy even when the reconstruction FOV does not include the whole of the subject 101.

(Composition Classification Image Data Generating Process)

When the non-metal image data $f_{Lin}$ is generated, the composition classification image data generating unit 217 carries out a composition classification image data generating process of generating composition classification image data from the non-metal image data $f_{Lin}$, which are initial image data (step S1106).

The composition classification image data generating unit 217 carries out a composition classification process $E_{sft}$ on the non-metal image data $f_{Lin}$, thereby generating composition classification image data $f_{prior}$, as shown in Expression (6) below.

$$f_{prior} = E_{sft}(f_{Lin}) \tag{6}$$

Herein, $E_{sft}$ indicates a soft tissue segmentation process (composition classification process).

In the composition classification process $E_{sft}$, firstly, the composition classification image data generating unit 217 carries out a threshold process with respect to the CT value of each pixel of the non-metal image data $f_{Lin}$, and classifies each pixel of the non-metal image data $f_{Lin}$ into, for example, four tissues, those being air, soft tissue, bone, and metal. Further, the composition classification image data generating unit 217 substitutes the CT value of each pixel in the two regions classified as air and soft tissue with an average CT value (HU) of the relevant region. Meanwhile, the composition classification image data generating unit 217 generates composition classification image data $f_{prior}$ for the two regions classified as bone and metal with the CT values unchanged. A commonly known smoothing filter processing may be carried out in advance on the non-metal image data in order to reduce the effect of noise or an artifact when carrying out the composition classification process. Also, a metal region classified as metal may be substituted with the average CT value of a region classified as soft tissue.

Also, a region classified as soft tissue need not necessarily be substituted with the average value.

It is sufficient that a composition structure is saved, and that the CT value is such that a fine oscillation component (an oscillation component of a frequency equal to or lower than a preset threshold) has been removed. This kind of CT value is obtained by, for example, applying an edge preserving image filter such as a TV (total variation) filter to the non-metal image data.

(Composition Classification Projection Data Generating Process)

When the composition classification image data $f_{prior}$ are generated, the composition classification projection data generating unit 218 carries out a composition classification projection data generating process (step S1107). The composition classification projection data generating unit 218 carries out the forward projection process R on the composition classification image data $f_{prior}$, thereby generating composition classification projection data $p_{prior}$, as shown in Expression (7) below.

$$p_{prior}=R(f_{prior}) \quad (7)$$

(Metal Penetration Region Substituting Process)

When the composition classification projection data $p_{prior}$ are generated, the metal penetration region substituting unit 219 carries out a metal penetration region substituting process (step S1108). In this embodiment, the metal penetration region substituting unit 219 substitutes the linear interpolation portion (metal penetration region) of the non-metal projection data $p_{Lin}$, obtained by carrying out a linear interpolation of the metal penetration region of the photographed projection data $p_{org}$, with a value (substitution value) that maintains continuity at a metal penetration region end portion boundary and indicates a smooth change, thereby generating primary corrected projection data $p_{fstc}$.

Herein, the substitution value is calculated from the composition classification projection data $p_{prior}$. As heretofore described, the metal penetration region is a region in the metal projection data $p_{mtl}$ whose projected value is equal to or greater than a preset threshold in the photographed projection data $p_{org}$.

Specifically, the metal penetration region substituting unit 219 carries out the interpolation process M on the metal penetration region of the composition classification projection data $p_{prior}$, obtains composition classification interpolation projection data M ($p_{prior}$) and adds a difference between the composition classification projection data $p_{prior}$ and composition classification interpolation projection data M ($p_{prior}$) to the non-metal projection data $p_{Lin}$, thereby generating the primary corrected projection data $p_{fstc}$. Specifically, the metal penetration region substituting unit 219 calculates the difference between data wherein the interpolation process M has been carried out on the metal penetration region in the composition classification projection data $p_{prior}$, in the same way as when generating the non-metal projection data $p_{Lin}$, and data before the linear interpolation, and adds the difference to the non-metal projection data $p_{Lin}$, thereby generating the primary corrected projection data $p_{fstc}$.

$$p_{fstc}=p_{prior}-M(p_{prior})+p_{Lin} \quad (8)$$

The interpolation process M, being the same kind of process as when generating the non-metal projection data $p_{Lin}$, is a process of interpolating a metal penetration region of composition classification projection data with projected values neighboring either end portion of the metal penetration region in a channel direction. Owing to this metal penetration region substituting process, corrected projection data that maintain continuity at a metal region boundary (a boundary between photographed projection data and composition classification projection data) can be obtained.

The metal penetration region substituting process (generation of primary corrected projection data) is not limited to the heretofore described method. For example, the following method may be used.

For example, the primary corrected projection data $P_{fstc}$ may be generated using a linear baseline shift approach shown in Expression (9) below. Specifically, firstly, the composition classification projection data $p_{prior}$ are subtracted from the photographed projection data $p_{org}$. Further, the same kind of interpolation process M as when generating non-metal projection data is carried out on the difference data obtained. Lastly, the composition classification projection data $p_{prior}$ are added to the projection data after the linear interpolation.

$$p_{fstc}=M(p_{org}-p_{prior})+p_{prior} \quad (9)$$

Also, for example, the primary corrected projection data $p_{fstc}$ may be generated using a method shown in Expression (10) below. Specifically, firstly, the photographed projection data $p_{org}$ are divided by the composition classification projection data $p_{prior}$. Further, the same kind of interpolation process M as when generating non-metal projection data is carried out on the post-division projection data obtained. Lastly, the projection data after the linear interpolation are multiplied by the composition classification projection data $p_{prior}$.

$$p_{fstc}=M(p_{org}/p_{prior}) \times p_{prior} \quad (10)$$

(Error Projection Data Generating Process)

When the primary corrected projection data $p_{fstc}$ are generated, the error projection data generating unit 220 carries out an error projection data generating process (step S1109). Specifically, the error projection data generating unit 220 subtracts the primary corrected projection data $p_{fstc}$ and metal projection data $p_{mtl}$ from the photographed projection data $p_{org}$, thereby generating error projection data $p_{err}$, as shown in Expression (11) below.

$$p_{err}=p_{org}-p_{fstc}-p_{mtl} \quad (11)$$

(High Frequency Component Extracting Process)

When the error projection data $p_{err}$ are generated, the high frequency component extracting unit 230 carries out a high frequency component extracting process (step S1110). In the high frequency component extracting process, the high frequency component extracting unit 230 smooths the error projection data $p_{err}$, obtains smoothed error projection data, and extracts a high frequency component from the error projection data $p_{err}$ by subtracting the smoothed error projection data from the error projection data $p_{err}$, thereby generating high frequency component projection data $p_{hfrq}$, as shown in Expression (12) below. The smoothing is carried out by a smoothing process using a smoothing filter S.

$$p_{hfrq} = p_{err} - S(p_{err}) \quad (12)$$

Herein, utilizing the fact that a metal artifact component (beam hardening component) corresponds to a low frequency component of the error projection data $p_{err}$ while a structure or discrete error component corresponds to a high frequency component, a structure or discrete error component is extracted by extracting the high frequency component from the error projection data $p_{err}$.

That is, the smoothing process S is carried out in order to separate noise, a structure, and a discrete error component from error projection data. A kernel of the smoothing filter S used in the smoothing process is, for example, one-dimensional in a channel direction, or two-dimensional, channel and linear. A kernel size is determined in accordance with pixel size or slice interval. For example, when the pixel size or slice interval is large, the kernel size is set to be large. By so doing, discrete errors caused by pixel size or slice interval can be effectively reduced.

(High Frequency Component Restoring Process)

When the high frequency component projection data $P_{hfrq}$ are generated, the high frequency component restoring unit 240 carries out a high frequency component restoring process (step S1111). The high frequency component restoring unit 240 multiplies each projected value of the high frequency component projection data $p_{hfrq}$ by a weight $W_{prj}$ ($p_{mtl}$) in accordance with a projected value of the metal projection data $p_{mtl}$, and adds to the primary corrected projection data $p_{fstc}$, thereby generating secondary corrected projection data $p_{corr}$ to which the high frequency component has been restored.

Specifically, the secondary corrected projection data $p_{corr}$ are calculated using Expression (13) below. That is, as heretofore described, the secondary corrected projection data $p_{corr}$ are calculated by multiplying the high frequency component projection data $p_{hfrq}$ by the weight $W_{prj}$ ($p_{mtl}$), and adding to the primary corrected projection data $p_{fstc}$.

$$p_{corr} = p_{fstc} + W_{prj}(p_{mtl})p_{hfrq} \quad (13)$$

At this time, the weight $W_{prj}$ ($p_{mtl}$) is determined, for example, as shown in Expression (14) below.

$$W_{prj}(p_{mtl}) = \begin{cases} 1 & p_{mtl} < t_{min} \\ 0 & p_{mtl} > t_{max} \\ \frac{t_{max} - p_{mtl}}{t_{max} - t_{min}} & \text{other} \end{cases} \quad (14)$$

Figure 7:
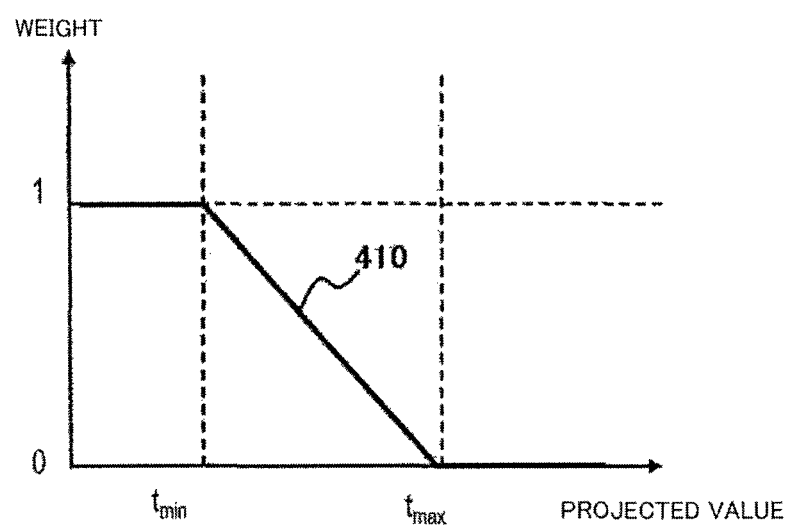
FIG. 7(a) is a graph showing a changing aspect of a weight of the first embodiment.
FIG. 7(b) is a graph showing a changing aspect of a weight of a modification example.
Figure 7:
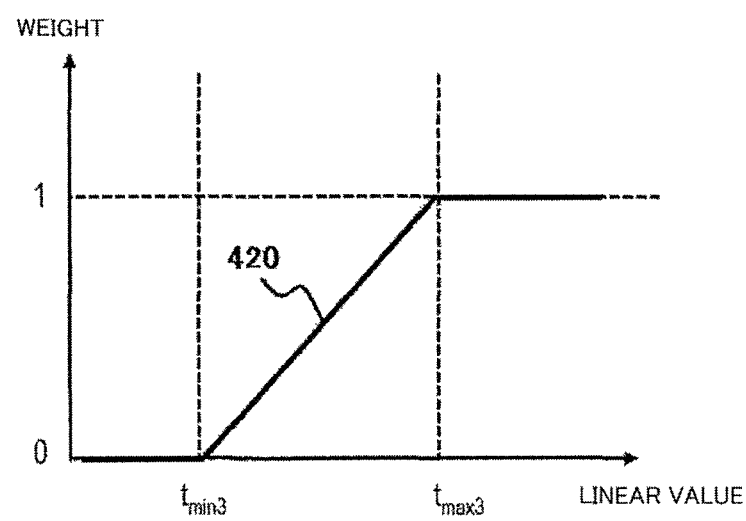

Herein, $t_{min}$ and $t_{max}$ satisfy $t_{min} < t_{max}$, and are projected values of the metal projection data $p_{mtl}$. These are thresholds for determining the weight $W_{prj}$ ($p_{mtl}$). A graph 410 showing a changing aspect of the weight $W_{prj}$ ($p_{mtl}$) is shown in FIG. 7(a).

A structure, noise, a slight metal artifact component, and a discrete error when carrying out a forward projection, are included in the high frequency component projection data $p_{hfrq}$. The weight $W_{prj}$ ($p_{mtl}$) is determined focusing on the fact that the metal artifact component size (metal artifact strength) is proportional to the metal attenuation magnitude, that is, the size of the metal projection data $p_{mtl}$.

That is, the weight $W_{prj}$ ($p_{mtl}$) is determined so as to be of a small value when the projected value of the metal projection data $p_{mtl}$ is large, and so as to be of a large value when the projected value is small, as shown in Expression (14) above. Because of this, a discrete error in a view in which the projected value of the metal projection data $p_{mtl}$ is small can be reduced. Also, noise of an extent such that there is no discordance in an image after reconstruction can be added, and a structure can be recovered.

A high frequency component restoring process such that error data or high frequency component data are calculated in standardized projection data shown in Expression (10) of the metal penetration region substituting process, or the like, may be carried out.

Figure 8:
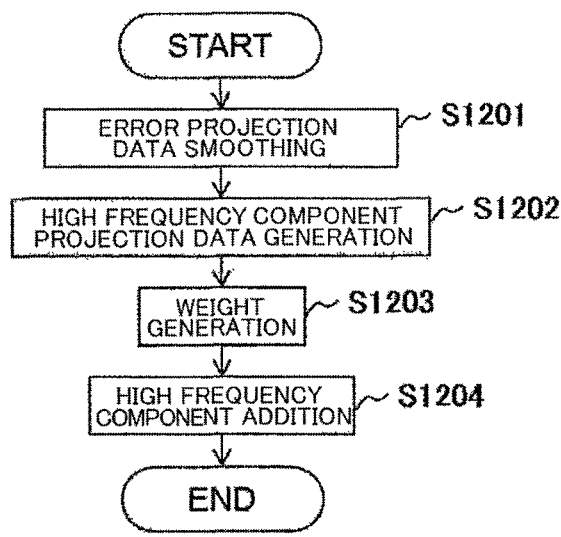
FIG. 8(a) is a flowchart of a high frequency component extracting and restoring process of the first embodiment.
FIG. 8(b) is a flowchart of a high frequency component extracting and restoring process of a third embodiment.
Figure 8:
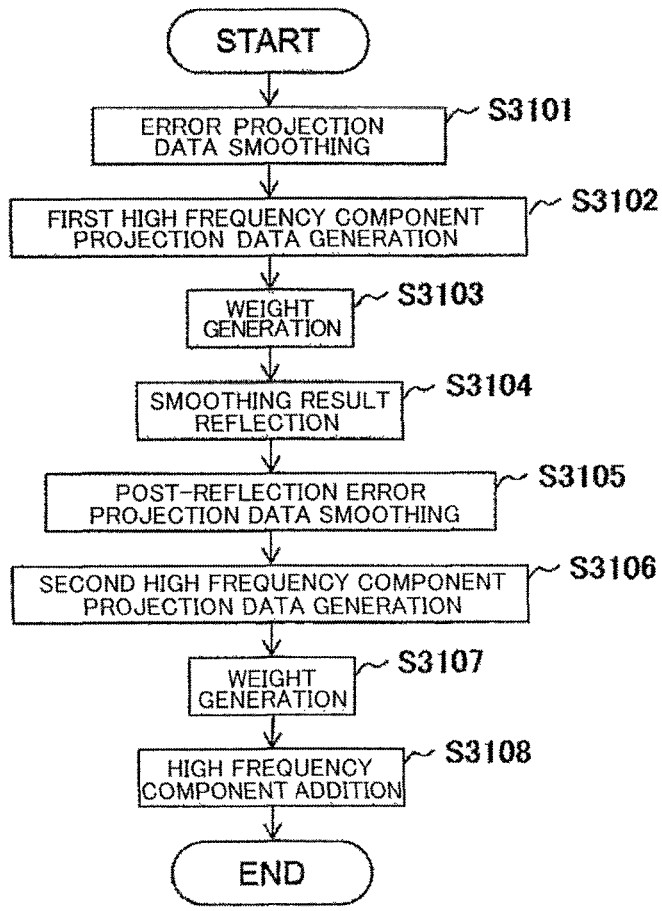

Herein, a flow of the high frequency component extracting process and high frequency component restoring process of this embodiment will be described, using FIG. 8(a).

Firstly, the high frequency component extracting unit 230 smooths the error projection data $p_{err}$ using the smoothing filter S, thereby generating smoothed error projection data (step S1201). Further, the high frequency component extracting unit 230 generates the high frequency component projection data $p_{hfrq}$ by subtracting the smoothed error projection data from the error projection data $p_{err}$ (step S1202).

Next, the high frequency component restoring unit 240 generates the weight $W_{prj}$ ($p_{mtl}$) in accordance with the projected value of the metal projection data $p_{mtl}$ (step S1203). Further, the high frequency component restoring unit 240 generates the secondary corrected projection data $p_{corr}$ by multiplying the high frequency component projection data $p_{hfrq}$ by the weight $W_{prj}$ ($p_{mtl}$) and adding to the primary corrected projection data $p_{fstc}$, that is, adding the high frequency component (step S1204).

(Metal Projection Data Adding Process)

When the secondary corrected projection data $p_{corr}$ are generated, the metal projection data adding unit 251 carries out a metal projection data adding process (step S1112). The metal projection data adding unit 251 adds the metal projection data $p_{mtl}$ to the secondary corrected projection data $p_{corr}$, thereby generating post-correction projection data $p_{corm}$, as shown in Expression (15) below.

$$p_{corm} = p_{corr} + p_{mtl} \quad (15)$$

By adding the metal projection data $p_{mtl}$ in the projection data in this way, an effect of the reconstruction filter can be reflected in a metal portion of a post-correction image, and an image with no discordance can be obtained.

(Post-correction Image Data Generating Process)

Lastly, the post-correction image data generating unit 250 carries out a post-correction image data generating process (step S1113). The post-correction image data generating unit 250 carries out the image reconstruction process $R^{-1}$ on the post-correction projection data $p_{corm}$, thereby generating post-correction image data $f_{corm}$, as shown in Expression (16) below.

$$f_{corr} = R^{-1}(p_{corm}) \quad (16)$$

At this time, image reconstruction is carried out using the desired reconstruction filter, the desired reconstruction FOV, and the desired reconstruction position.

Post-correction image data 310, obtained by a reconstruction process by the reconstruction arithmetic apparatus 132 of this embodiment from photographed projection data wherein the image shown in FIG. 3(a) has been reconstructed, are shown in FIG. 3(b). As shown in the diagram, it is clear that the metal artifact (301 in FIG. 3(a)) is suppressed by the reconstruction process of this embodiment, and that the structure remains.

As heretofore described, the X-ray CT apparatus of this embodiment includes the X-ray tube (X-ray generating device) 111 that emits an X-ray, the X-ray detector 113, disposed in a position opposing the X-ray tube across the subject 101, that detects an X-ray that penetrates the subject 101, the central controller 125 that controls the X-ray tube and X-ray detector 113 so as to carry out a CT scan on the subject 101, the signal processor 116 that obtains photographed projection data from an X-ray detected in the X-ray detector 113, and a reconstruction arithmetic apparatus 132 that generates a reconstructed image from the photographed projection data.

Further, the reconstruction arithmetic apparatus 132 includes the primary corrected projection data generating unit 210 that generates primary corrected projection data from the photographed projection data by removing at least one portion of an artifact component caused by metal, the error projection data generating unit 220 that subtracts the primary corrected projection data from the photographed projection data, thereby generating error projection data, the high frequency component extracting unit 230 that extracts a high frequency component from the error projection data, and generates the high frequency component as high frequency component projection data, the high frequency component restoring unit 240 that generates secondary corrected projection data by multiplying the high frequency component projection data by a weight in accordance with preset projection data and adding to the primary corrected projection data, and the post-correction image data generating unit 250 that generates post-correction image data based on the secondary corrected projection data.

The primary corrected projection data generating unit 210 includes the initial image data generating unit 211 that generates initial image data from the photographed projection data, the composition classification image data generating unit 217 that generates composition classification image data from the initial image data, the composition classification projection data generating unit 218 that carries out a forward projection on the composition classification image data, thereby generating composition classification projection data, and the metal penetration region substituting unit 219 that substitutes a projected value of a metal penetration region of the photographed projection data with a projected value of the relevant metal penetration region of the composition classification projection data, thereby generating the primary corrected projection data, wherein the composition classification image data generating unit 217 generates the composition classification image data by classifying each pixel of the initial image data into a preset multiple of tissues, and substituting with a preset CT value for each composition.

The initial image data are non-metal image data, and the initial image data generating unit 211 includes the photographed image data generating unit 212 that reconstructs the photographed projection data, thereby generating photographed image data, the metal image data generating unit 213 that generates metal image data obtained by extracting a metal region from the photographed image data, the metal projection data generating unit 214 that carries out a forward projection on the metal image data, thereby generating metal projection data, the non-metal projection data generating unit 215 that carries out an interpolation process on a metal penetration region of the photographed projection data, thereby generating non-metal projection data, and the non-metal image data generating unit 216 that reconstructs the non-metal projection data, thereby generating the non-metal image data, wherein the metal penetration region is a region in which a projected value of the metal projection data is equal to or greater than a predetermined threshold.

In this way, according to this embodiment, the primary corrected projection data $p_{fstc}$ are generated by interpolating a metal penetration region in projection data using neighboring data. Further, a high frequency component corresponding to a structure is extracted from the error projection data $p_{err}$ pertaining to the photographed projection data $p_{org}$ of the primary corrected projection data $p_{fstc}$, and added to the primary corrected projection data $p_{fstc}$. Because of this, information on the structure can be recovered. Also, fine noise in a metal region periphery can also be recovered, whereby a more natural image can be obtained.

Furthermore, when the high frequency component is added to the primary corrected projection data $p_{fstc}$, weighting is carried out in accordance with the size of the projected value of the metal projection data $p_{mtl}$. Because of this, the stronger a metal artifact is, the more a contribution can be suppressed. Because of this, even when a metal artifact component is contained in the extracted high frequency component, restoration thereof can be suppressed. Furthermore, a discrete error in a view in which the projected value of the metal projection data $p_{mtl}$ is small is reduced.

Also, the primary corrected projection data $p_{fstc}$ are calculated based on metal projection data calculated from a value that is a CT value corresponding to soft tissue subtracted from a CT value of a metal region in photographed image data reconstructed from photographed projection data. Consequently, the projected value of a metal penetration region in the primary corrected projection data $p_{fstc}$ is near to an actual value.

An existing method is such that when correcting a metal penetration region in photographed projection data, all tissues coinciding with a metal portion in a sinogram are substituted with composition classification projection data. A structure that cannot be segmentalized in composition classification image data, such as a structure of bone hidden by the metal artifact, or soft tissue that cannot be correctly segmentalized, is lost in an image reconstructed from projection data after the substitution.

According to this embodiment, however, the high frequency component restoring process is such that a high frequency component of the error projection data $p_{err}$ is extracted, and the extracted high frequency component is weighted and added to the primary corrected projection data $p_{fstc}$, whereby a lost structure component not contained in the composition classification projection data $p_{prior}$ is restored. Because of this, loss of composition coinciding with a metal region in a sinogram can be alleviated in this embodiment.

Also, according to conventional art, substitution is carried out with forward projection data compiled from a composition classification image with no noise when correcting a metal penetration region in photographed projection data, because of which a metal periphery of a post-correction image is a discordant image with no noise. According to this embodiment, however, the high frequency component projection data $p_{hfrq}$ including a noise component is added to the primary corrected projection data $p_{fstc}$ in the high frequency component restoring process, because of which the problem is resolved, and an image with no discordance even in a metal periphery is obtained.

Also, according to conventional art, when there is an error in a projected value of composition classification projected data due to noise, a beam hardening effect, an artifact, a CT value adjustment error, segmentation accuracy, or the like, when correcting a metal penetration region in photographed projection data, discontinuity occurs in a portion switched with a corrected projection, and a streak artifact may appear from a metal margin.

According to this embodiment, however, composition classification interpolation projection data wherein a linear interpolation process has been carried out on a metal penetration region in the composition classification projection data $p_{prior}$ are subtracted from the composition classification projection data $p_{prior}$ and added to the non-metal projection data $p_{Lin}$ in the metal penetration region substituting process. That is, substitution is carried out so that a place in which a linear interpolation process has been carried out on a metal region is continued smoothly. Because of this, discontinuity of projection data can be improved, and a streak artifact at a metal margin can be restricted.

Also, for example, when a desired reconstruction slice interval is large (for example, a 5 mm thick image when a slice thickness is large), or when a desired FOV size is large (for example, a 450 mm FOV size), when generating metal projection data, conventional art is such that a forward projection process is carried out on a metal image with rough pixels. Consequently, a discrete error occurs in the metal projection data $p_{mtl}$, and this becomes an artifact in the post-correction image data $f_{corm}$ eventually obtained.

At this time, according to the conventional art, when generating a metal image with fine pixels differing from the desired slice thickness and FOV size in order to generate highly accurate metal projection data, the metal image data added last have to be reconstructed again with the desired reconstruction slice thickness and desired FOV size, which involves an increase in calculation time.

Furthermore, according to conventional art, a discrete error also occurs in the composition classification projection data $p_{prior}$ when compiling composition classification projection data, and this becomes an artifact (for example, a windmill-form artifact) in the post-correction image data $f_{corm}$.

According to this embodiment, however, as heretofore described, discrete errors are reduced, because of which an artifact in the post-correction image data $f_{corm}$ can be suppressed, even when the reconstruction interval is wide (when the slice thickness is large), or when the FOV is large.

Also, according to this embodiment, a specific filter with little noise can be used when generating the non-metal image data $f_{Lin}$ when generating a composition classification image. According to conventional art, segmentation accuracy worsens depending on the reconstruction filter used for smoothing, and by extension, the desired correction accuracy may not be obtained. In this embodiment, however, the worsening of segmentation accuracy can be alleviated.

Also, according to this embodiment, the non-metal image data $f_{Lin}$ are reconstructed with a full FOV. Because of this, the whole of the subject 101 is included in the image, and the subject 101 does not protrude from the image. Therefore, composition classification can be carried out appropriately when generating subsequent composition classification image data.

Also, for example, when the reconstruction FOV is small and the subject protrudes from the image (when not the whole of the subject is included in the image) when compiling a composition classification projection, conventional art is such that subject information is lost, the composition classification projection data are minimally evaluated, and a large error occurs. According to this embodiment, however, this kind of error is suppressed, and a good result is obtained.

Second Embodiment

Next, a second embodiment of the invention will be described. In this embodiment, the non-metal projection data $p_{Lin}$ are substituted with the secondary corrected projection data $p_{corr}$ every time the secondary corrected projection data $p_{corr}$ are obtained, and an iterative process is carried out.

Figure 9:
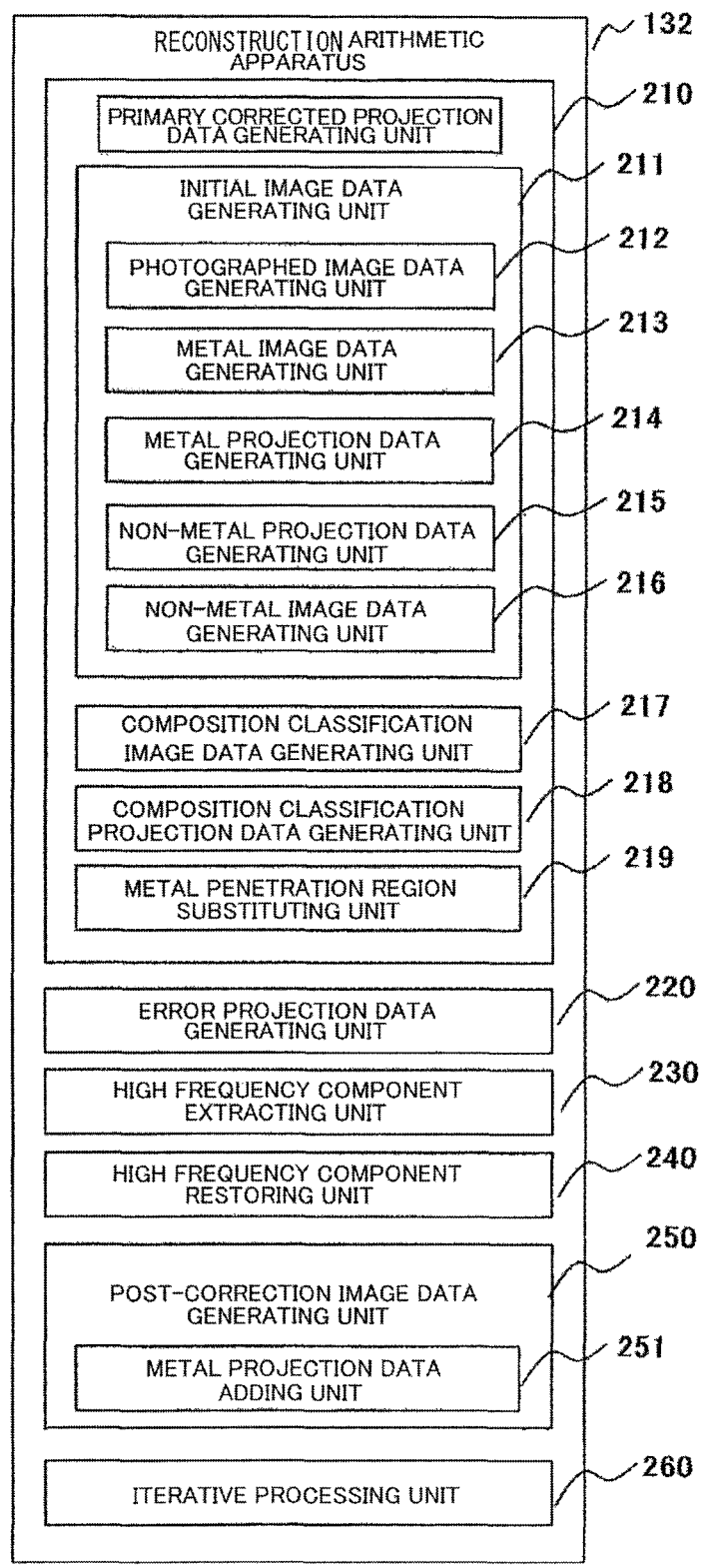
FIG. 9 is a functional block diagram of a reconstruction arithmetic apparatus of a second embodiment.

An X-ray CT apparatus of this embodiment has basically the same configuration as the X-ray CT apparatus 100 of the first embodiment. However, an iterative process is carried out in a reconstruction process accompanying a correction of a metal artifact. Because of this, the reconstruction arithmetic apparatus 132 of this embodiment further includes an iterative processing unit 260 that carries out an iterative process, as shown in FIG. 9. Hereafter, this embodiment will be described focusing on a configuration differing from the first embodiment.

(Iterative Process)

The iterative processing unit 260 of this embodiment substitutes the non-metal projection data $p_{Lin}$ with the secondary corrected projection data every time the secondary corrected projection data $p_{corr}$ are generated, and repeats generation of the primary corrected projection data $p_{fstc}$ and secondary corrected projection data $p_{corr}$ a preset number of times.

That is, when the non-metal projection data $p_{Lin}$ are generated, the iterative processing unit 260 of this embodiment repeats a preset number of times from the non-metal image data generating process by the non-metal image data generating unit 216 to the secondary corrected projection data $p_{corr}$ generating process by the high frequency component restoring unit 240. At this time, the non-metal projection data $p_{Lin}$ are substituted with the secondary corrected projection data $p_{corr}$ generated by the high frequency component restoring unit 240, and the process is repeated. Processing details of each repeated process are the same as in the first embodiment.

Figure 10:
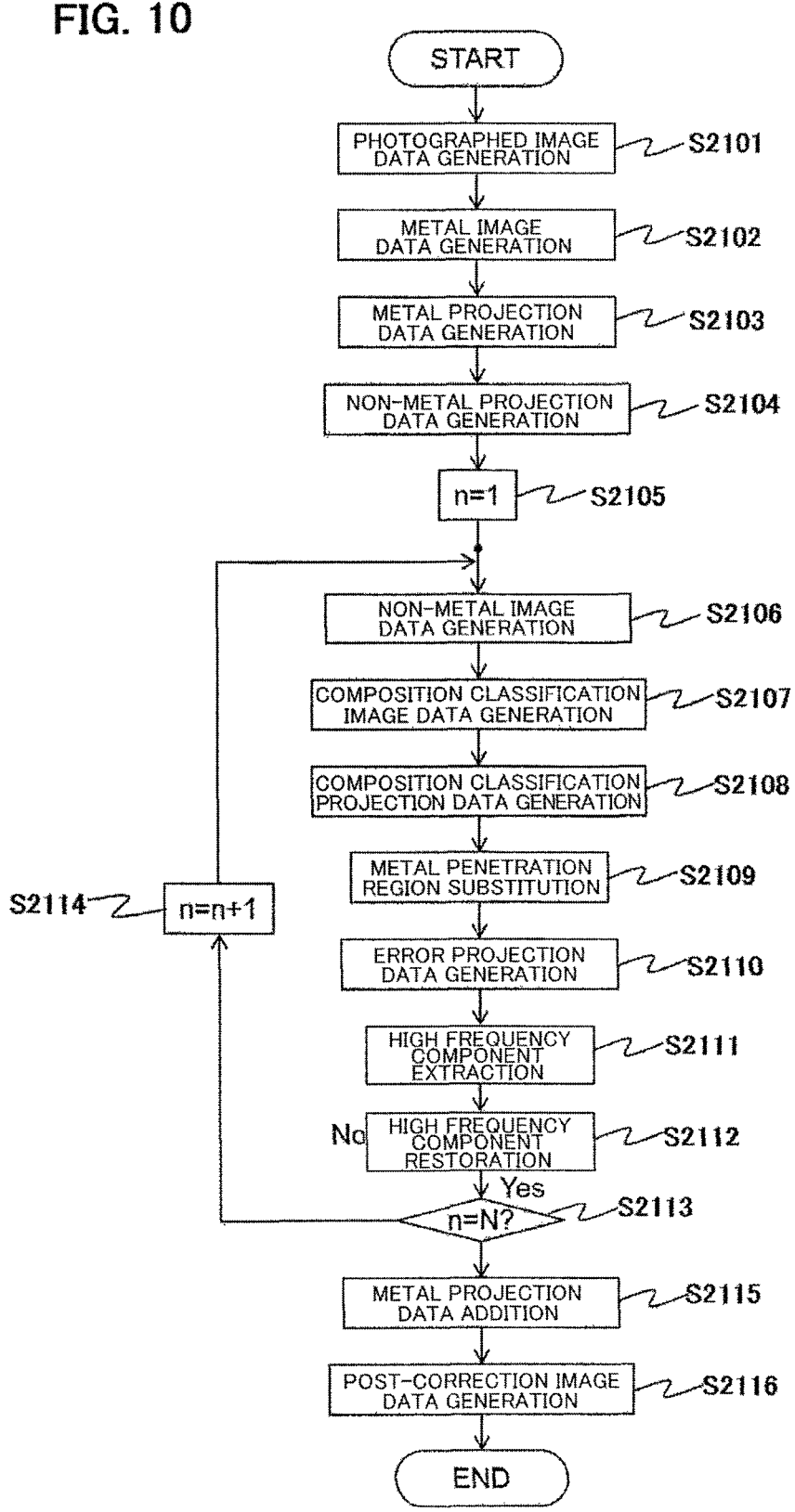
FIG. 10 is a flowchart of a reconstruction process of the second embodiment.
Figure 11:
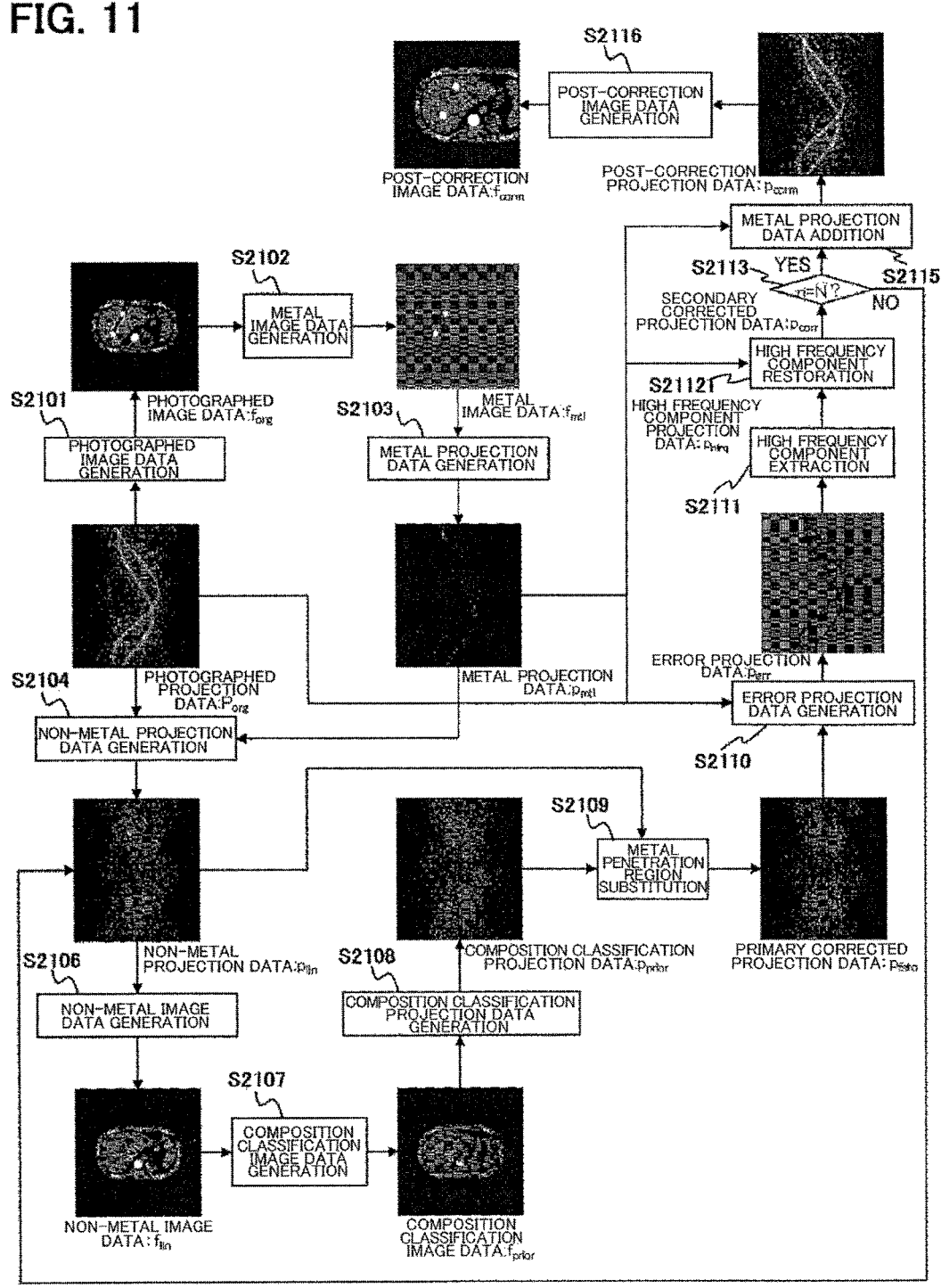
FIG. 11 is an illustration for describing the reconstruction process of the second embodiment.

Hereafter, a flow of the processes of this embodiment will be described using FIG. 10 and FIG. 11, focusing on a place differing from the first embodiment. FIG. 10 is a process flow of a reconstruction process accompanying a correction of a metal artifact by the reconstruction arithmetic apparatus 132 of this embodiment, and FIG. 11 is an illustration for describing the flow of the reconstruction process.

A photographed image data generating process by the photographed image data generating unit 212 (step S2101), a metal image data generating process by the metal image data generating unit 213 (step S2102), a metal projection data generating process by the metal projection data generating unit 214 (step S2103), and a non-metal projection data generating process by the non-metal projection data generating unit 215 (step S2104) are the same as in the first embodiment, because of which a description will be omitted.

Taking a number of repetitions to be N and a repetition counter to be n, the iterative processing unit 260, firstly, initializes the repetition counter n (n=1) (step S2105).

The non-metal image data generating unit 216 carries out the image reconstruction process $R^{-1}$ on the non-metal projection data $p_{Lin}$, thereby generating non-metal image data $f_{Lin}^{n}$ from which the metal has been removed, as shown in Expression (17) below (step S2106).

$$f_{Lin}^{n} = R^{-1}(p_{corr}^{n-1}) \qquad (17)$$

n and n−1 to the upper right of the non-metal image data $f_{Lin}^{n}$ and secondary corrected projection data $p_{corr}$ respectively indicate the number of repetitions of generating the data. That is, n is appended to the upper right of image data or projection data generated for an $n^{th}$ repetition. Herein, it is taken that $p_{corr}^{0} = p_{Lin}$.

The composition classification image data generating unit 217 generates composition classification image data $f_{prior}{}^n$ from the non-metal image data $f_{Lin}{}^n$, as shown in Expression (18) below (step S2107).

$$f_{prior}{}^n = E_{sfi}(f_{Lin}{}^n) \quad (18)$$

The composition classification projection data generating unit 218 generates composition classification projection data $p_{prior}{}^n$ from the composition classification image data $f_{prior}{}^n$, as shown in Expression (19) below (step S2108).

$$p_{prior}{}^n = R(f_{prior}{}^n) \quad (19)$$

The metal penetration region substituting unit 219 calculates the difference between data wherein the interpolation process M has been carried out on the metal penetration region in the composition classification projection data $p_{prior}{}^n$, in the same way as when generating non-metal projection data, and data before the linear interpolation, and adds the difference to the non-metal projection data $p_{Lin}$ (herein, $p_{corr}{}^{n-1}$) thereby generating primary corrected projection data $P_{fstc}{}^n$, as shown in Expression (20) below (step S2109).

$$p_{fstc}{}^n = p_{prior}{}^n - M(p_{prior}{}^n) + p_{corr}{}^{n-1} \quad (20)$$

Of course, in this embodiment too, the methods according to Expression (21) and Expression (22) below may be used in the generation of the primary corrected projection data $p_{fstc}{}^n$, in the same way as in the first embodiment.

$$p_{fstc}{}^n = M(p_{org} - p_{prior}{}^n) + p_{prior}{}^n \quad (21)$$

$$p_{fstc}{}^n = M(p_{org}/p_{prior}{}^n) \times p_{prior}{}^n \quad (22)$$

The error projection data generating unit 220 subtracts the primary corrected projection data $P_{fstc}{}^n$ and metal projection data $p_{mtl}$ from the photographed projection data $p_{org}$, thereby generating error projection data $p_{err}{}^n$, as shown in Expression (23) below (step S2110).

$$p_{err}{}^n = p_{org} - p_{fstc}{}^n - p_{mtl} \quad (23)$$

The high frequency component extracting unit 230 extracts a high frequency component from the error projection data $p_{err}{}^n$, thereby generating high frequency component projection data $p_{hfrq}{}^n$ (step S2111).

In this embodiment too, the high frequency component is extracted by the smoothing process S being carried out on the error projection data $p_{err}{}^n$, and the post-smoothing data being subtracted from the error projection data $p_{err}{}^n$, as shown in Expression (24) below.

$$p_{hfrg}{}^n = p_{err}{}^n - S(p_{err}{}^n) \quad (24)$$

Further, the high frequency component restoring unit 240 carries out a high frequency component restoring process (step S2112). Herein, the high frequency component restoring unit 240 multiplies each projected value of the generated high frequency component projection data $p_{hfrq}{}^n$ by the weight $W_{prj}(p_{mtl})$ in accordance with a projected value of the metal projection data $p_{mtl}$, and adds to the primary corrected projection data $p_{fstc}{}^n$, thereby generating secondary corrected projection data $p_{corr}{}^n$ to which the high frequency component has been restored.

At this time, the secondary corrected projection data $p_{corr}$ are calculated using Expression (25) below. That is, as heretofore described, the secondary corrected projection data $p_{corr}$ are calculated by multiplying the high frequency component projection data $p_{hfrq}{}^n$ by the weight $W_{prj}(p_{mtl})$, and adding to the primary corrected projection data $p_{fstc}{}^n$. Herein, the weight $W_{prj}(p_{mtl})$ is determined as shown in, for example, Expression (14).

$$p_{corr}{}^n = p_{fstc}{}^n + W_{prj}(p_{mtl}) p_{hfrq}{}^n \quad (25)$$

Herein, the weight $W_{prj}(p_{mtl})$ used is the same as in the first embodiment.

Subsequently, the iterative processing unit 260 compares the number of repetitions n with the number of repetitions N (step S2113) and when N is not reached, increases n by 1 (step S2114), and repeats the process. Meanwhile, when the process is finished N times, the iterative processing unit 260 advances the process to a metal projection data adding process and onward. The subsequent processes are the same as in the first embodiment.

That is, the metal projection data adding unit 251 adds the metal projection data $p_{mtl}$ to the secondary corrected projection data $p_{corr}$ after N repetitions of the process, thereby generating the post-correction projection data $p_{corm}$, as shown in Expression (26) below (step S2115).

$$p_{corm} = p_{corr}{}^N + p_{mtl} \quad (26)$$

Further, the post-correction image data generating unit 250 carries out the image reconstruction process $R^{-1}$ on the post-correction projection data $p_{corm}$, thereby generating the post-correction image data $f_{corm}$, as shown in Expression (27) below (step S2116).

$$f_{corr} = R^{-1}(p_{corm}) \quad (27)$$

As heretofore described, the X-ray CT apparatus 100 of this embodiment includes, in the same way as in the first embodiment, the X-ray tube (X-ray generating device) 111, X-ray detector 113, central controller 125, signal processor 116, and reconstruction arithmetic apparatus 132. Further, the reconstruction arithmetic apparatus 132 includes the primary corrected projection data generating unit 210, error projection data generating unit 220, high frequency component extracting unit 230, high frequency component restoring unit 240, post-correction image data generating unit 250, and iterative processing unit 260.

The primary corrected projection data generating unit 210 includes the initial image data generating unit 211, composition classification image data generating unit 217, composition classification projection data generating unit 218, and metal penetration region substituting unit 219, and the initial image data generating unit 211 includes the photographed image data generating unit 212, metal image data generating unit 213, metal projection data generating unit 214, non-metal projection data generating unit 215, and non-metal image data generating unit 216.

Further, the iterative processing unit 260 substitutes the non-metal projection data with the secondary corrected projection data every time the secondary corrected projection data are generated, and repeats generation of the primary corrected projection data and secondary corrected projection data a preset number of times.

In this way, according to this embodiment, a configuration the same as that of the first embodiment is included, because of which the same advantages as in the first embodiment are obtained. Furthermore, according to this embodiment, the secondary corrected projection data $p_{corr}$ are used as non-metal projection data, and an iterative process is carried out. At this time, non-metal projection data generated by an interpolation process such that a metal portion is easily removed include a large interpolation error, but by the non-metal projection data being substituted with secondary corrected projection data having comparatively few errors, the non-metal projection data accuracy improves, and the accuracy of the continuously generated secondary corrected projection data $p_{corr}$ also improves. As a result, the accuracy of the post-correction projection data $p_{corm}$ generated based on this also increases, and the eventual post-correction image data $f_{corm}$ improve.

Third Embodiment

Next, a third embodiment of the invention will be described. In this embodiment, a smoothing process is carried out multiple times when extracting a high frequency component. At this time, a filter used may be changed.

The X-ray CT apparatus 100 of this embodiment has basically the same configuration as in the first embodiment.

However, as the high frequency component extracting process differs, the processes of the high frequency component extracting unit 230 and high frequency component restoring unit 240 differ. Hereafter, this embodiment will be described focusing on a configuration differing from the first embodiment.

In this embodiment, the high frequency component extracting unit 230 uses two or more differing kinds of smoothing filter, and the high frequency component restoring unit 240 generates a multiplying weight using projection data in accordance with the kind of smoothing filter used.

The high frequency component extracting unit 230 of this embodiment, in the same way as in the first embodiment, extracts a high frequency component from the error projection data $p_{err}$, thereby generating the high frequency component projection data $p_{hfrq}$. The extraction of the high frequency component, in the same way as in the first embodiment, is carried out by implementing a smoothing process. In this embodiment, however, the smoothing process is repeated multiple times.

Also, the high frequency component restoring unit 240 of this embodiment, in the same way as in the first embodiment, multiplies each projected value of the high frequency component projection data $p_{hfrq}$ by a weight $W_{prj}$ (p) in accordance with a projected value of a preset kind of projection data p, and adds to the primary corrected projection data $p_{fstc}$, thereby generating the secondary corrected projection data $p_{corr}$.

The high frequency component extracting process by the high frequency component extracting unit 230 and the high frequency component restoring process by the high frequency component restoring unit 240 in this embodiment will be described using a specific example, in accordance with FIG. 8(b). Herein, as one example, a description will be given with a case wherein smoothing is carried out twice using two differing kinds of smoothing filter as an example. Smoothing may also be carried out multiple Limes using the same smoothing filter.

For example, it is taken that a first smoothing filter $S_1$ using a smoothing kernel with a size of 1 in the view direction, 3 in the column direction, 3 in the channel direction is used in a first smoothing process, and a second smoothing filter $S_2$ using a smoothing kernel with a size of 3 in the view direction, 5 in the column direction, 5 in the channel direction 5 is used in a second smoothing process.

Firstly, the high frequency component extracting unit 230 applies the first smoothing filter $S_1$ to the error projection data $p_{err}$, thereby generating smoothed error projection data $S_1(p_{err})$ (step S3101). Further, by subtracting the smoothed error projection data $S_1(p_{err})$ from the error projection data $p_{err}$, the high frequency component extracting unit 230 generates first high frequency component projection data $p_{hfrq1}$ (step S3102). The processes of step S3101 and step S3102 are expressed in Expression (28) below.

$$p_{hfrq1} = p_{err} - S_1(p_{err}) \quad (28)$$

Further, the high frequency component restoring unit 240 selects the photographed projection data $p_{org}$ as projection data used in weight calculation, and generates a weight $W_{prj}$ ($p_{org}$) in accordance with a projected value of the photographed projection data $p_{org}$, as shown in Expression (29) below (step S3103).

$$W_{prj}(p_{org}) = \begin{cases} 1 & p_{org} < t_{min\ 1} \\ 0 & p_{org} > t_{max\ 1} \\ \dfrac{t_{max\ 1} - p_{org}}{t_{max\ 1} - t_{min\ 1}} & \text{other} \end{cases} \quad (29)$$

$t_{min1}$ and $t_{max1}$ satisfy $t_{min1} < t_{max1}$, and are projected values of the photographed projection data $p_{org}$. These are thresholds for determining a first weight $W_{prj}(p_{org})$.

In the first smoothing process using the first smoothing filter $S_1$, mainly a noise component is extracted. Generally, noise in the projection data depends on the size of the projected value of the photographed projection data $p_{org}$. When attenuation in a metal portion is ignored, noise in the projection data depends on the size of the composition classification projection data $p_{prior}$. Because of this, the first high frequency component projection data $p_{hfrq1}$, in which a noise component is predominant, are such that the projected value of the photographed projection data $p_{org}$ and the first weight $W_{prj}$ ($p_{org}$) in accordance with the composition classification projection data $p_{prior}$ are multiplied.

Further, the high frequency component restoring unit 240 generates post-reflection error projection data $p_{err1}$ by multiplying the first high frequency component projection data $p_{hfrq1}$ by the generated weight $W_{prj}(p_{org})$ and subtracting from the error projection data $p_{err}$, as shown in Expression (30) below (step S3104). By so doing, the high frequency component restoring unit 240 reflects the extracted first high frequency component projection data $p_{hfrq1}$ in the error projection data $p_{err}$.

$$p_{err1} = p_{err} - W_{prj}(p_{org})p_{hfrq1} \quad (30)$$

Next, the high frequency component extracting unit 230 applies the second smoothing filter $S_2$ to the post-reflection error projection data $p_{err1}$, thereby generating smoothed error projection data $S_2(p_{err1})$ (step S3105). Further, by subtracting the smoothed error projection data $S_2(p_{err1})$ from the error projection data $p_{err1}$, the high frequency component extracting unit 230 generates second high frequency component projection data $p_{hfrq2}$ (step S3106). The processes of step S3105 and step S3106 are expressed in Expression (31) below.

$$p_{hfrq2} = p_{err1} - S_2(p_{err1}) \quad (31)$$

Further, the high frequency component restoring unit 240 selects the metal projection data $p_{mtl}$ as projection data used in weight calculation, and generates a weight $W_{prj}$ ($p_{mtl}$) in accordance with a projected value of the metal projection data $p_{mtl}$, as shown in Expression (32) below (step S3107).

$$W_{prj}(p_{mtl}) = \begin{cases} 1 & p_{mtl} < t_{min\ 2} \\ 0 & p_{mtl} > t_{max\ 2} \\ \dfrac{t_{max\ 2} - p_{mtl}}{t_{max\ 2} - t_{min\ 2}} & \text{other} \end{cases} \quad (32)$$

Herein, $t_{min2}$ and $t_{max2}$ satisfy $t_{min2} < t_{max2}$ and are projected values of the metal projection data $p_{mtl}$. These are thresholds for determining a second weight $W_{prj}(p_{mtl})$.

In the second smoothing process using the second smoothing filter $S_2$, mainly a structure component, a discrete error component, and a metal artifact component are extracted. The metal artifact component depends on the size of the projected value of the metal projection data $p_{mtl}$. Because of this, the second high frequency component projection data $p_{hfrq2}$ including the metal artifact component are multiplied by the second weight $W_{prj}(p_{mtl})$ which is in accordance with the size of the projected value of the metal projection data $p_{mtl}$.

Further, the high frequency component restoring unit 240, in the same way as in the first embodiment, calculates the secondary corrected projection data $p_{corr}$ to which the high frequency component has been restored by multiplying the extracted first high frequency component projection data $p_{hfrq1}$ by the first weight $W_{prj}(p_{org})$ which is in accordance with the photographed projection data $p_{org}$, multiplying the extracted second high frequency component projection data $p_{hfrq2}$ by the second weight $W_{prj}(p_{mtl})$, which is in accordance with the metal projection data $p_{mtl}$, and adding to the primary corrected projection data $P_{fstc}$, as shown in Expression (33) below (step S3108).

$$p_{corr} = p_{fstc} + W_{prj}(p_{org})p_{hfrq1} + W_{prj}(p_{mtl})p_{hfrq2} \quad (33)$$

The heretofore described process is such that either of the first smoothing process and second smoothing process may be carried out first.

Also, as other processes are the same as in the first embodiment, a description will be omitted here.

As heretofore described, the X-ray CT apparatus 100 of this embodiment includes, in the same way as in the first embodiment, the X-ray tube (X-ray generating device) 111, X-ray detector 113, central controller 125, signal processor 116, and reconstruction arithmetic apparatus 132. Further, the reconstruction arithmetic apparatus 132 includes the primary corrected projection data generating unit 210, error projection data generating unit 220, high frequency component extracting unit 230, high frequency component restoring unit 240, post-correction image data generating unit 250, and iterative processing unit 260.

Further, the primary corrected projection data generating unit 210 includes the initial image data generating unit 211, composition classification image data generating unit 217, composition classification projection data generating unit 218, and metal penetration region substituting unit 219, and the initial image data generating unit 211 includes the photographed image data generating unit 212, metal image data generating unit 213, metal projection data generating unit 214, non-metal projection data generating unit 215, and non-metal image data generating unit 216.

Further, the high frequency component extracting unit 230 uses two or more differing kinds of smoothing filter when smoothing the error projection data, and the high frequency component restoring unit 240 generates the multiplying weight using projection data in accordance with the kind of smoothing filter used.

According to this embodiment, a configuration the same as that of the first embodiment is included, because of which the same advantages as in the first embodiment are obtained. Furthermore, according to this embodiment, the high frequency component extracting process and high frequency component restoring process are such that the high frequency component is extracted using a multiple of differing smoothing filters. Further, the post-extraction high frequency component is multiplied by a weight based on projection data in accordance with characteristics of the relevant component, thereby restoring the high frequency component. Because of this, a metal artifact can be reduced while reducing noise due to a radiation dose deficiency, and a structure hidden in metal projection data, or a discrete error component, can be efficiently recovered.

In this embodiment, in order to simplify the description, a simple smoothing filter such that the extent of smoothing changes only in accordance with kernel size is used as a smoothing filter. However, the smoothing filter used is not limited to this. Any smoothing filter having more non-linear characteristics, such as a median filter, a Gaussian filter, a TV filter, or a filter using a wavelet process, may be used. As the smoothing process of this embodiment is carried out in order to extract a trend component in error projection data, it is sufficient that a filter can achieve this object.

Also, in this embodiment, a description has been given with a case in which the embodiment is applied to the first embodiment as an example, but this embodiment may also be applied to the second embodiment. That is, the non-metal projection data $p_{Lin}$ may be substituted with the second corrected projection data $p_{corr}$ obtained, and the iterative process repeated a predetermined number of times.

Modification Example

In each of the embodiments, the initial image data may be photographed image data.

In this case, the initial image data generating unit 211 includes the photographed image data generating unit 212 that reconstructs the photographed projection data $p_{org}$, thereby generating the photographed image data $f_{org}$, but need not include the other metal image data generating unit 213, metal projection data generating unit 214, non-metal projection data generating unit 215, or non-metal image data generating unit 216.

Furthermore, in each of the embodiments, the post-correction image data generating unit 250 adds (restores) metal information to the projection data (secondary corrected projection data $p_{corr}$) when generating the post-correction image data $f_{corm}$ from the secondary corrected projection data $p_{corr}$. However, this method is not limiting.

For example, the metal information may be added after reconstruction. In this case, the post-correction image data generating unit 250 obtains secondary post-correction image data by reconstructing the secondary corrected projection data $p_{corr}$, and adds the CT value of a photographed image data metal region to the secondary post-correction image data, thereby obtaining the post-correction image data $f_{corm}$. The CT value of the metal region is obtained when compiling the metal image data $f_{mtl}$.

Furthermore, the post-correction image data generating unit 250 need not add metal information when generating the post-correction image data $f_{corm}$ from the secondary corrected projection data $p_{corr}$. This is because metal information is not needed when a metal portion is not a diagnosis target in a reconstructed image.

Also, in each of the embodiments, a projected value of the photographed projection data $p_{org}$, metal projection data $p_{mtl}$, or composition classification projection data $p_{prior}$ is used unchanged in weight calculation. However, a weight calculation method is not limited to this. For example, the weight $W_{prj}(p)$ may be determined in accordance with a linear value p wherein an inverse logarithmic transformation has been carried out on a projected value of each item of projection data, as shown in Expression (34) below. That is, the weight $W_{prj}(p)$ is determined so that a weight value becomes smaller the greater the linear value p.

$$W_{prj}(p) = \begin{cases} 0 & p < t_{min\ 3} \\ 1 & p > t_{max\ 3} \\ \dfrac{p - t_{min\ 3}}{t_{max\ 3} - t_{min\ 3}} & \text{other} \end{cases} \quad (34)$$

Herein, $t_{min3}$ and $t_{max3}$ satisfy $t_{min3} < t_{max3}$, and are the linear value p wherein an inverse logarithmic transformation has been carried out. These are thresholds for determining the weight $W_{prj}(p)$. A graph 420 of a changing aspect of the weight in this case is shown in FIG. 7(b).

Also, in each of the embodiments, it is described that the reconstruction arithmetic apparatus 132 is included in the X-ray CT apparatus 100, but this is not limiting. For example, the reconstruction arithmetic apparatus 132 may be structured on an information processing apparatus independent of the X-ray CT apparatus 100, including a CPU, a memory, and a storage device, with the information processing apparatus being able to receive data from the signal processor 116.

From the description above relating to the various embodiments of the invention, it is clear that the object of the invention is achieved. As indicated together with describing in detail the embodiments of the invention, these are intended to be only descriptions and exemplifications of examples of embodiments of the invention, and are not limiting.

REFERENCE SIGNS LIST

100 X-ray CT apparatus, 101 Subject, 111 X-ray generating device, 112 High voltage generating device, 113 X-ray detector, 114 Collimator, 115 Pre-amplifier, 116 Signal processor, 117 Bed movement measuring device, 118 Drive device, 121 X-ray controller, 122 Scanner controller, 123 Collimator controller, 124 Bed controller, 125 Central controller, 130 Operating unit, 131 Arithmetic device, 132 Reconstruction arithmetic apparatus, 133 Image processor, 141 Input/output device, 142 Input device, 143 Display device, 144 Storage device, 150 Bed, 210 Primary corrected projection data generating unit, 211 Initial image data generating unit, 212 Photographed image data generating unit, 213 Metal image data generating unit, 214 Metal projection data generating unit, 215 Non-metal projection data generating unit, 216 Non-metal image data generating unit, 217 Composition classification image data generating unit, 218 Composition classification projection data generating unit, 219 Metal penetration region substituting unit, 220 Error projection data generating unit, 230 High frequency component extracting unit, 240 High frequency component restoring unit, 250 Post-correction image data generating unit, 251 Metal projection data adding unit, 260 Iterative processing unit, 300 Reconstructed image, 301 Metal artifact, 310 Post-correction image data, 410 Weight graph, 420 Weight graph

The invention claimed is:

1. A reconstruction arithmetic apparatus, comprising:
a primary corrected projection data generating unit that generates primary corrected projection data from photographed projection data, which are projection data obtained by a CT scan, by removing at least one portion of an artifact component caused by metal;
an error projection data generating unit that subtracts the primary corrected projection data from the photographed projection data, thereby generating error projection data;
a high frequency component extracting unit that extracts a high frequency component from the error projection data, and generates the high frequency component as high frequency component projection data;
a high frequency component restoring unit that generates secondary corrected projection data by multiplying the high frequency component projection data by a weight in accordance with preset projection data and adding to the primary corrected projection data;
and a post-correction image data generating unit that generates post-correction image data based on the secondary corrected projection data.

2. The reconstruction arithmetic apparatus according to claim 1, wherein the primary corrected projection data generating unit includes:
an initial image data generating unit that generates initial image data from the photographed projection data;
a composition classification image data generating unit that generates composition classification image data from the initial image data; a composition classification projection data generating unit that carries out a forward projection on the composition classification image data, thereby generating composition classification projection data; and
a metal penetration region substituting unit that substitutes a projected value of a metal penetration region of the photographed projection data with a projected value of the relevant metal penetration region of the composition classification projection data, thereby generating the primary corrected projection data, wherein
the composition classification image data generating unit generates the composition classification image data by classifying each pixel of the initial image data into a preset multiple of tissues, and substituting with a preset CT value for each composition.

3. The reconstruction arithmetic apparatus according to claim 2, wherein
the initial image data are non-metal image data, and
the initial image data generating unit includes:
a photographed image data generating unit that reconstructs the photographed projection data, thereby generating photographed image data; a metal image data generating unit that generates metal image data obtained by extracting a metal region from the photographed image data;
a metal projection data generating unit that carries out a forward projection on the metal image data, thereby generating metal projection data;
a non-metal projection data generating unit that carries out an interpolation process on a metal penetration region of the photographed projection data, thereby generating non-metal projection data;
and a non-metal image data generating unit that reconstructs the non-metal projection data, thereby generating the non-metal image data, wherein
the metal penetration region is a region in which a projected value of the metal projection data is equal to or greater than a predetermined threshold.

4. The reconstruction arithmetic apparatus according to claim 3, wherein
the metal penetration region substituting unit carries out the interpolation process on the metal penetration region of the composition classification projection data, obtains composition classification interpolation projection data, and adds a difference between the composition classification projection data and composition classification interpolation projection data to the non-metal projection data, thereby generating the primary corrected projection data.

5. The reconstruction arithmetic apparatus according to claim 3, wherein
the post-correction image data generating unit adds the metal projection data to the secondary corrected projection data, generates post-correction projection data, and obtains the post-correction image data by reconstructing the post-correction projection data.

6. The reconstruction arithmetic apparatus according to claim 3, wherein
the post-correction image data generating unit obtains secondary post-correction image data by reconstructing the secondary corrected projection data, and adds a CT value of the metal region of the photographed image data to the secondary post-correction image data, thereby obtaining the post-correction image data.

7. The reconstruction arithmetic apparatus according to claim 3, further comprising
an iterative processing unit that substitutes the non-metal projection data with the secondary corrected projection data every time the secondary corrected projection data are generated, and repeats generation of the primary corrected projection data and secondary corrected projection data a preset number of times.

8. The reconstruction arithmetic apparatus according to claim 3, wherein
a reconstruction FOV used when the non-metal image data generating unit generates the non-metal image data is a maximum FOV, and a reconstruction center position is a center of rotation when carrying out the CT scan.

9. The reconstruction arithmetic apparatus according to claim 2, wherein
the initial image data are photographed image data, and
the initial image data generating unit includes a photographed image generating unit that reconstructs the photographed projection data, thereby generating the photographed image data.

10. The reconstruction arithmetic apparatus according to claim 2, wherein the preset multiple of tissues include air, soft tissue, and metal, and the composition classification image data generating unit substitutes a CT value of an air region classified as the air with an average CT value of the air region, substitutes a CT value of a soft tissue region classified as the soft tissue with an average CT value of the soft tissue region, and substitutes a CT value of a metal region classified as the metal with an average CT value of the soft tissue region.

11. The reconstruction arithmetic apparatus according to claim 2, wherein
the preset multiple of tissues include soft tissue and metal, and
the composition classification image data generating unit saves a composition structure of a CT value of a soft tissue region classified as the soft tissue and takes the CT value to be a value wherein an oscillation component equal to or lower than a preset. threshold has been removed, and takes a CT value of a metal region classified as the metal to be a CT value of the soft tissue.

12. The reconstruction arithmetic apparatus according to claim 1, wherein
the high frequency component extracting unit smooths the error projection data, obtains smoothed error projection data, and subtracts the smoothed error projection data from the error projection data, thereby generating the high frequency component projection data.

13. The reconstruction arithmetic apparatus according to claim 12, wherein
the high frequency component extracting unit uses a smoothing filter when smoothing the error projection data.

14. The reconstruction arithmetic apparatus according to claim 13, wherein
the high frequency component extracting unit uses two or more smoothing filters, and
the high frequency component restoring unit generates the weight using projection data in accordance with a kind of smoothing filter used.

15. The reconstruction arithmetic apparatus according to claim 1, wherein
a value of the weight is set to increase further the further a projected value increases in a predetermined projected value range.

16. The reconstruction arithmetic apparatus according to claim 1, wherein,
using a linear value wherein an inverse logarithmic conversion has been carried out on each projected value of the projection data, a value of the weight is set to decrease further the further the linear value increases in a predetermined linear value range.

17. An X-ray CT apparatus, comprising:
an X-ray tube that emits an X-ray;
an X-ray detector, disposed in an opposing position across a subject, that detects an X-ray that penetrates the subject;
a central controller that controls the X-ray tube and X-ray detector so as to carry out a CT scan on the subject;
a signal processor that obtains photographed projection data from an X-ray detected by the X-ray detector; and
the reconstruction arithmetic apparatus according to claim 1 that generates a reconstructed image from the photographed projection data.

18. An X-ray CT image generation method, comprising steps of:
generating primary corrected projection data from photographed projection data, which are projection data obtained by a CT scan, by removing at least one portion of an artifact component caused by metal;
subtracting the generated primary corrected projection data from the photographed projection data, thereby generating error projection data;
extracting a high frequency component from the error projection data, and generating the high frequency component as high frequency component projection data;
generating secondary corrected projection data by multiplying by a weight in accordance with projection data set in advance in the high frequency component projection data, and adding to the primary corrected projection data;
and reconstructing post-correction image data based on the secondary corrected projection data.

* * * * *